United States Patent
Hess et al.

(10) Patent No.: US 10,342,520 B2
(45) Date of Patent: Jul. 9, 2019

(54) ARTICULATING SURGICAL DEVICES AND LOADERS HAVING STABILIZING FEATURES

(71) Applicant: Ethicon Endo-Surgery, LLC, Guaynabo, PR (US)

(72) Inventors: Christopher J. Hess, Blue Ash, OH (US); Frederick E. Shelton, IV, Hillsboro, OH (US); Ryan A. Bledsoe, Cincinnati, OH (US); Monica L. Zeckel, Cincinnati, OH (US); Jeffrey L. Savage, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 856 days.

(21) Appl. No.: 14/836,235

(22) Filed: Aug. 26, 2015

(65) Prior Publication Data

US 2017/0055971 A1 Mar. 2, 2017

(51) Int. Cl.
*A61B 17/00* (2006.01)
*A61B 17/29* (2006.01)
*A61B 90/00* (2016.01)

(52) U.S. Cl.
CPC ........ *A61B 17/00234* (2013.01); *A61B 17/29* (2013.01); *A61B 17/2909* (2013.01);
(Continued)

(58) Field of Classification Search
CPC .......... A61B 17/29; A61B 2017/00362; A61B 2017/2927; A61B 2017/2931;
(Continued)

(56) References Cited

U.S. PATENT DOCUMENTS 2,922,669 A 1/1960 Hansen
3,043,309 A 7/1962 McCarthy
(Continued)

FOREIGN PATENT DOCUMENTS

DE 101 49 421 A1 4/2003
EP 1 709 900 A1 10/2006
(Continued)

OTHER PUBLICATIONS

International Search Report dated Mar. 21, 2011; International Application No. PCT/US2010/051812 (7 pages).
(Continued)

*Primary Examiner* — Boniface N Nganga
(74) *Attorney, Agent, or Firm* — Mintz Levin Cohn Ferris Glovsky and Popeo, P.C.

(57) ABSTRACT

Surgical devices and methods are described. The loading devices can include an elongate shaft extending distally from a housing and a hinge can be disposed between the elongate shaft and an articulating distal portion. The articulating distal portion can hold an end effector to be loaded onto a surgical device. The loading device can have features for stabilizing and holding the distal portion at a particular angular position relative to the elongate shaft, such as washers having protrusions that seat in corresponding recesses formed in the hinge. During articulation of the distal portion, an articulation rack can be advanced which can deform the protrusions on the washers. The washers can rotate and seat in the recesses at the next angular position and change the degree of articulation. The deformable washer and corresponding recesses can apply a biasing force that holds the articulating distal portion in a desired angled position.

17 Claims, 13 Drawing Sheets

(52) U.S. Cl.
CPC .............. *A61B 2017/00371* (2013.01); *A61B 2017/00424* (2013.01); *A61B 2017/00876* (2013.01); *A61B 2017/2919* (2013.01); *A61B 2017/2925* (2013.01); *A61B 2017/2931* (2013.01); *A61B 2017/2946* (2013.01); *A61B 2090/0813* (2016.02)

(58) Field of Classification Search
CPC .. A61B 2017/2946; A61B 2017/00371; A61B 2017/00424; A61B 2017/00876; A61B 2017/2919; A61B 2017/2925; A61B 17/00234; A61B 17/2909; A61B 2090/0813
See application file for complete search history.

(56) References Cited

U.S. PATENT DOCUMENTS

| | | | |
|---|---|---|---|
| 3,358,676 A | 12/1967 | Frei et al. | |
| 3,710,399 A | 1/1973 | Hurst | |
| 3,893,448 A | 7/1975 | Brantigan | |
| 3,906,217 A | 9/1975 | Lackore | |
| 3,988,535 A | 10/1976 | Hickman et al. | |
| 4,047,136 A | 9/1977 | Satto | |
| 4,063,561 A | 12/1977 | McKenna | |
| 4,099,192 A | 7/1978 | Aizawa et al. | |
| 4,278,077 A | 7/1981 | Mizumoto | |
| 4,384,584 A | 5/1983 | Chen | |
| 4,585,282 A | 4/1986 | Bosley | |
| 4,597,390 A | 7/1986 | Mulhollan et al. | |
| 4,655,746 A | 4/1987 | Daniels et al. | |
| 5,052,402 A | 10/1991 | Bencini et al. | |
| 5,201,743 A | 4/1993 | Haber et al. | |
| 5,282,806 A | 2/1994 | Haber et al. | |
| 5,286,255 A | 2/1994 | Weber | |
| 5,308,357 A | 5/1994 | Lichtman | |
| 5,314,424 A | 5/1994 | Nicholas | |
| 5,330,502 A | 7/1994 | Hassler et al. | |
| 5,352,219 A | 10/1994 | Reddy | |
| 5,392,917 A | 2/1995 | Alpern et al. | |
| 5,417,203 A | 5/1995 | Tovey et al. | |
| 5,441,059 A | 8/1995 | Dannan | |
| 5,468,250 A | 11/1995 | Paraschac et al. | |
| 5,502,698 A | 3/1996 | Mochizuki | |
| 5,507,297 A | 4/1996 | Slater et al. | |
| 5,540,648 A | 7/1996 | Yoon | |
| 5,562,655 A | 10/1996 | Mittelstadt et al. | |
| 5,578,052 A | 11/1996 | Koros et al. | |
| 5,593,402 A | 1/1997 | Patrick | |
| 5,613,937 A | 3/1997 | Garrison et al. | |
| 5,618,303 A | 4/1997 | Marlow et al. | |
| 5,716,326 A | 2/1998 | Dannan | |
| 5,762,255 A | 6/1998 | Chrisman et al. | |
| 5,792,165 A | 8/1998 | Klieman et al. | |
| 5,810,877 A | 9/1998 | Roth et al. | |
| 5,881,615 A | 3/1999 | Dahl et al. | |
| 5,928,263 A | 7/1999 | Hoogeboom | |
| 5,972,012 A * | 10/1999 | Ream ............... | A61B 17/32002 604/22 |
| 5,980,455 A | 11/1999 | Daniel et al. | |
| 6,024,748 A | 2/2000 | Manzo et al. | |
| 6,059,719 A | 5/2000 | Yamamoto et al. | |
| 6,099,537 A | 8/2000 | Sugai et al. | |
| 6,159,200 A | 12/2000 | Verdura et al. | |
| 6,309,397 B1 | 10/2001 | Julian et al. | |
| 6,315,789 B1 | 11/2001 | Cragg | |
| 6,419,688 B1 | 7/2002 | Bacher et al. | |
| 6,471,172 B1 | 10/2002 | Lemke et al. | |
| 6,589,211 B1 | 7/2003 | MacLeod | |
| 6,595,984 B1 | 7/2003 | DeGuillebon | |
| 6,626,824 B2 | 9/2003 | Ruegg et al. | |
| 6,635,071 B2 | 10/2003 | Boche et al. | |
| 6,723,043 B2 | 4/2004 | Kleeman et al. | |
| 6,770,081 B1 | 8/2004 | Cooper et al. | |
| 6,776,165 B2 | 8/2004 | Jin | |
| 6,827,712 B2 | 12/2004 | Tovey et al. | |
| 6,860,878 B2 | 3/2005 | Brock | |
| 6,869,395 B2 | 3/2005 | Page et al. | |
| 6,884,213 B2 | 4/2005 | Raz et al. | |
| 6,936,003 B2 | 8/2005 | Iddan | |
| 6,942,674 B2 | 9/2005 | Belef et al. | |
| 6,986,738 B2 | 1/2006 | Glukhovsky et al. | |
| 6,994,708 B2 | 2/2006 | Manzo | |
| 7,039,453 B2 | 5/2006 | Mullick et al. | |
| 7,042,184 B2 | 5/2006 | Oleynikov et al. | |
| 7,066,879 B2 | 6/2006 | Fowler et al. | |
| 7,083,579 B2 | 8/2006 | Yokoi et al. | |
| 7,122,028 B2 | 10/2006 | Looper et al. | |
| 7,125,403 B2 | 10/2006 | Julian et al. | |
| 7,169,104 B2 | 1/2007 | Ueda et al. | |
| 7,199,545 B2 | 4/2007 | Oleynikov et al. | |
| 7,211,094 B2 | 5/2007 | Gannoe et al. | |
| 7,241,290 B2 | 7/2007 | Doyle et al. | |
| 7,297,142 B2 | 11/2007 | Brock | |
| 7,331,967 B2 | 2/2008 | Lee et al. | |
| 7,429,259 B2 | 9/2008 | Cadeddu et al. | |
| 7,448,993 B2 | 11/2008 | Yokoi et al. | |
| 7,559,887 B2 | 7/2009 | Dannan | |
| 7,566,331 B2 | 7/2009 | Looper et al. | |
| 7,604,642 B2 | 10/2009 | Brock | |
| 7,651,471 B2 | 1/2010 | Yokoi et al. | |
| 7,666,181 B2 | 2/2010 | Abou El Kheir | |
| 7,678,043 B2 | 3/2010 | Gilad | |
| 7,691,103 B2 | 4/2010 | Fernandez et al. | |
| 7,691,126 B2 | 4/2010 | Bacher | |
| 7,699,835 B2 | 4/2010 | Lee et al. | |
| 7,722,599 B2 | 5/2010 | Julian et al. | |
| 7,862,553 B2 | 1/2011 | Ewaschuk | |
| 7,894,882 B2 | 2/2011 | Mullick et al. | |
| 7,901,398 B2 | 3/2011 | Stanczak et al. | |
| 8,021,358 B2 | 9/2011 | Doyle et al. | |
| 8,038,612 B2 | 10/2011 | Paz | |
| 8,052,636 B2 | 11/2011 | Moll et al. | |
| 8,057,502 B2 | 11/2011 | Maliglowka et al. | |
| 8,088,062 B2 | 1/2012 | Zwolinski | |
| 8,128,643 B2 | 3/2012 | Aranyi et al. | |
| 8,182,414 B2 | 5/2012 | Handa et al. | |
| 8,187,166 B2 | 5/2012 | Kuth et al. | |
| 8,377,044 B2 | 2/2013 | Coe et al. | |
| 8,397,335 B2 | 3/2013 | Gordin et al. | |
| 8,398,544 B2 | 3/2013 | Altamirano | |
| 8,409,076 B2 | 4/2013 | Pang et al. | |
| 8,475,361 B2 | 7/2013 | Barlow et al. | |
| 8,518,024 B2 | 8/2013 | Williams et al. | |
| 8,623,011 B2 | 1/2014 | Spivey | |
| 8,636,648 B2 | 1/2014 | Gazdzinski | |
| 8,721,539 B2 | 5/2014 | Shohat et al. | |
| 8,764,735 B2 | 7/2014 | Coe et al. | |
| 8,764,769 B1 | 7/2014 | Rodriguez-Navarro et al. | |
| 8,845,661 B2 | 9/2014 | D'Arcangelo et al. | |
| 9,142,527 B2 | 9/2015 | Lee et al. | |
| 9,282,879 B2 | 3/2016 | Farin et al. | |
| 9,308,011 B2 | 4/2016 | Chao et al. | |
| 9,408,628 B2 | 8/2016 | Altamirano | |
| 9,451,937 B2 | 9/2016 | Parihar | |
| 2001/0051766 A1 | 12/2001 | Gazdzinski | |
| 2003/0060702 A1 | 3/2003 | Kuth et al. | |
| 2003/0114731 A1 | 6/2003 | Cadeddu et al. | |
| 2004/0093039 A1 | 5/2004 | Schumert | |
| 2004/0133235 A1 | 7/2004 | Bacher | |
| 2004/0152941 A1 | 8/2004 | Asmus et al. | |
| 2004/0199982 A1 | 10/2004 | Wang-Lee et al. | |
| 2005/0033354 A1 | 2/2005 | Montalvo et al. | |
| 2005/0085697 A1 | 4/2005 | Yokoi et al. | |
| 2005/0119640 A1 | 6/2005 | Sverduk et al. | |
| 2005/0131396 A1 | 6/2005 | Stanczak et al. | |
| 2005/0165449 A1 | 7/2005 | Cadeddu et al. | |
| 2005/0215983 A1 | 9/2005 | Brock | |
| 2005/0250984 A1 | 11/2005 | Lam et al. | |
| 2005/0272972 A1 | 12/2005 | Iddan | |
| 2005/0272974 A1 | 12/2005 | Iddan | |
| 2005/0273139 A1 | 12/2005 | Krauss et al. | |
| 2005/0288555 A1 | 12/2005 | Binmoeller | |
| 2006/0079933 A1 | 4/2006 | Hushka et al. | |

(56) References Cited

U.S. PATENT DOCUMENTS

| | | |
|---|---|---|
| 2006/0149135 A1 | 7/2006 | Paz |
| 2006/0184161 A1 | 8/2006 | Maahs et al. |
| 2006/0190035 A1 | 8/2006 | Hushka et al. |
| 2006/0195015 A1 | 8/2006 | Mullick et al. |
| 2006/0229592 A1 | 10/2006 | Yokoi et al. |
| 2006/0258905 A1 | 11/2006 | Kaji et al. |
| 2007/0010709 A1 | 1/2007 | Reinschke |
| 2007/0049966 A1 | 3/2007 | Bonadio et al. |
| 2007/0073247 A1 | 3/2007 | Ewaschuk |
| 2007/0093792 A1 | 4/2007 | Julian et al. |
| 2007/0123748 A1 | 5/2007 | Meglan |
| 2007/0156015 A1 | 7/2007 | Gilad |
| 2007/0255100 A1 | 11/2007 | Barlow et al. |
| 2007/0255273 A1 | 11/2007 | Fernandez et al. |
| 2007/0270651 A1 | 11/2007 | Gilad et al. |
| 2007/0270895 A1 | 11/2007 | Nobis et al. |
| 2007/0299387 A1 | 12/2007 | Williams et al. |
| 2008/0004656 A1 | 1/2008 | Livneh |
| 2008/0015413 A1 | 1/2008 | Barlow et al. |
| 2008/0015552 A1 | 1/2008 | Doyle et al. |
| 2008/0045003 A1 | 2/2008 | Lee et al. |
| 2008/0140090 A1 | 6/2008 | Aranyi et al. |
| 2008/0142005 A1 | 6/2008 | Schnell |
| 2008/0154299 A1 | 6/2008 | Livneh |
| 2008/0242939 A1 | 10/2008 | Johnston |
| 2008/0243106 A1 | 10/2008 | Coe et al. |
| 2008/0287926 A1 | 11/2008 | Abou El Kheir |
| 2008/0312499 A1 | 12/2008 | Handa et al. |
| 2009/0005636 A1 | 1/2009 | Pang et al. |
| 2009/0005638 A1 | 1/2009 | Zwolinski |
| 2009/0206124 A1 | 8/2009 | Hall et al. |
| 2009/0209947 A1 | 8/2009 | Gordin et al. |
| 2010/0249700 A1 | 9/2010 | Spivey |
| 2011/0040322 A1 | 2/2011 | Major |
| 2011/0087265 A1 | 4/2011 | Nobis et al. |
| 2011/0087266 A1 | 4/2011 | Conlon et al. |
| 2011/0087267 A1 | 4/2011 | Spivey et al. |
| 2011/0087269 A1* | 4/2011 | Stokes .................. A61B 17/29 606/206 |
| 2011/0115891 A1 | 5/2011 | Trusty |
| 2011/0208007 A1 | 8/2011 | Shohat et al. |
| 2011/0230869 A1 | 9/2011 | Altamirano |
| 2011/0288560 A1 | 11/2011 | Shohat et al. |
| 2012/0050960 A1 | 3/2012 | Chien |
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078290 A1 | 3/2012 | Nobis et al. |
| 2012/0078291 A1 | 3/2012 | Nobis et al. |
| 2012/0083826 A1 | 4/2012 | Chao et al. |
| 2012/0088965 A1 | 4/2012 | Stokes et al. |
| 2012/0089093 A1 | 4/2012 | Trusty |
| 2012/0095298 A1 | 4/2012 | Stefanchik et al. |
| 2012/0095456 A1 | 4/2012 | Schechter et al. |
| 2012/0259325 A1 | 10/2012 | Houser et al. |
| 2012/0310220 A1* | 12/2012 | Malkowski .......... A61B 17/29 606/1 |
| 2012/0316575 A1 | 12/2012 | Farin et al. |
| 2013/0138091 A1 | 5/2013 | Coe et al. |
| 2013/0138092 A1 | 5/2013 | Hinchliffe et al. |
| 2013/0331646 A1 | 12/2013 | Pell et al. |
| 2014/0005474 A1 | 1/2014 | Farin et al. |
| 2014/0066711 A1 | 3/2014 | Farin et al. |
| 2014/0088569 A1 | 3/2014 | Parihar et al. |
| 2014/0088637 A1 | 3/2014 | Parihar et al. |
| 2014/0088638 A1 | 3/2014 | Parihar |
| 2014/0243799 A1 | 8/2014 | Parihar |
| 2014/0243800 A1 | 8/2014 | Parihar |
| 2014/0276666 A1* | 9/2014 | Malkowski .......... A61B 17/29 606/1 |
| 2014/0277018 A1 | 9/2014 | Parihar |
| 2014/0378953 A1 | 12/2014 | Coe et al. |
| 2015/0088191 A1 | 3/2015 | Coe et al. |
| 2017/0055970 A1 | 3/2017 | Hess et al. |

FOREIGN PATENT DOCUMENTS

| | | |
|---|---|---|
| JP | 2005-261734 A | 9/2005 |
| JP | 2008-518716 A | 6/2008 |
| WO | 2008/015666 A2 | 2/2008 |
| WO | 2010/060436 A1 | 6/2010 |
| WO | 2010/081482 A1 | 7/2010 |
| WO | 2010/111319 A1 | 9/2010 |
| WO | 2010/114634 A1 | 10/2010 |
| WO | 2011/044353 A1 | 4/2011 |
| WO | 2011/089565 A1 | 7/2011 |
| WO | 2012/035524 A2 | 3/2012 |
| WO | 2012/040183 A1 | 3/2012 |
| WO | 2012/112622 A2 | 8/2012 |
| WO | 2012/126967 A2 | 9/2012 |
| WO | 2013/007764 A2 | 1/2013 |
| WO | 2013/048963 A2 | 4/2013 |
| WO | 2014/052177 A1 | 4/2014 |
| WO | 2014145595 A2 | 9/2014 |

OTHER PUBLICATIONS

International Preliminary Report dated Apr. 19, 2012; International Application No. PCT/US2010/051812; (10 pages).
International Search Report dated Mar. 2, 2012; International Application No. PCT/US2011/050198 (7 pages).
International Preliminary Report dated Mar. 14, 2013; International Application No. PCT/US2011/050198 (10 pages).
International Search Report dated Dec. 12, 2011; International Application No. PCT/US2011/052327 (5 pages).
International Preliminary Report dated Apr. 4, 2013; International Application No. PCT/US2011/052327 (9 pages).
International Search Report dated Apr. 3, 2013; International Application No. PCT/US2012/056900 (3 pages).
International Preliminary Report dated Apr. 10, 2014; International Application No. PCT/US2012/056900 (8 pages).
International Search Report dated Dec. 20, 2013; International Application No. PCT/US2013/060803 (3 pages).
International Preliminary Report dated Apr. 9, 2015; International Application No. PCT/US2013/060803 (9 pages).
International Search Report dated May 28, 2014; International Application No. PCT/US2014/015738 (4 pages).
International Preliminary Report on Patentability dated Sep. 11, 2015; International Application No. PCT/US2014/015738 (12 pages).
U.S. Application as filed on Oct. 9, 2009 for U.S. Appl. No. 12/576,529 (18 pages).

* cited by examiner

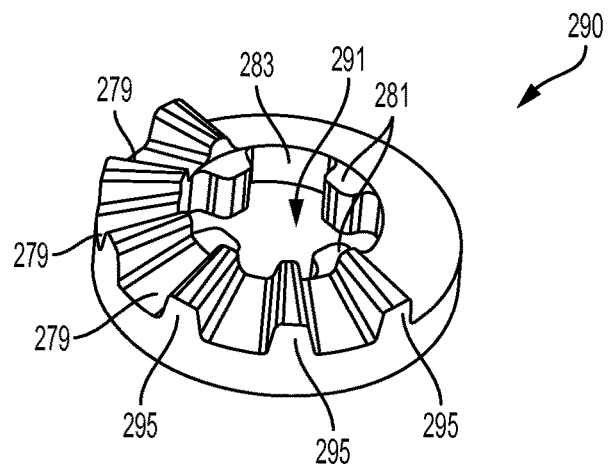
FIG. 6C
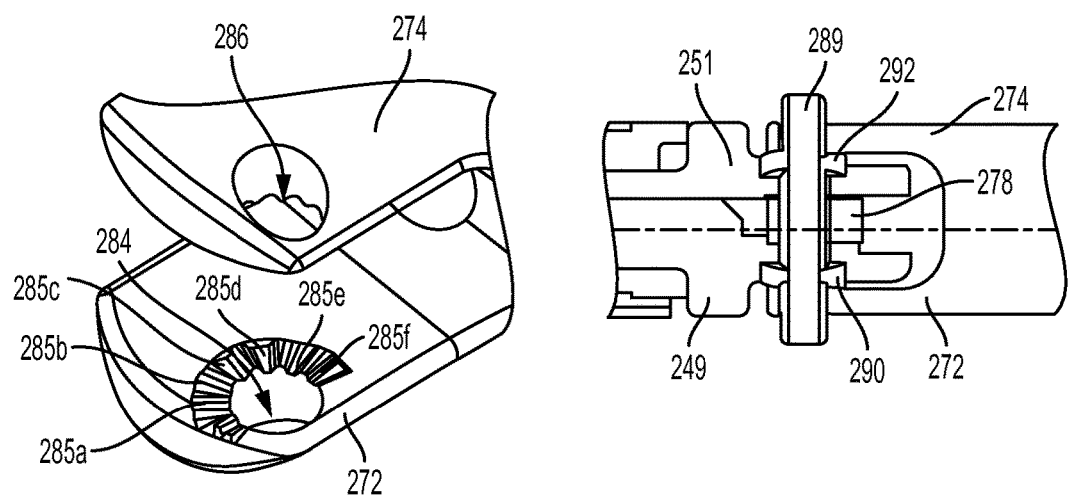
FIG. 6D
FIG. 6E

ARTICULATING SURGICAL DEVICES AND LOADERS HAVING STABILIZING FEATURES

CROSS-REFERENCE TO RELATED APPLICATIONS

The present application is related to U.S. application Ser. No. 14/836,069, filed Aug. 26, 2015, entitled "Surgical Device Having Actuator Biasing and Locking Features," the disclosure of which is incorporated herein by reference in its entirety.

FIELD

The present application relates to articulating surgical devices and loaders having stabilizing features.

BACKGROUND

Surgical procedures are often used to treat and cure a wide range of diseases, conditions, and injuries. Surgery often requires access to internal tissue through open surgical procedures or endoscopic surgical procedures. The term "endoscopic" refers to all types of minimally invasive surgical procedures including laparoscopic, arthroscopic, natural orifice intraluminal, and natural orifice transluminal procedures.

Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to manipulate the patient's internal tissue while maintaining pneumoperitoneum. For example, trocars are often used to provide a port through which endoscopic surgical instruments are passed. Trocars generally have an instrument seal which prevents the insufflatory fluid from escaping while an instrument is positioned in the trocar.

Various surgical instruments can be configured to manipulate tissue during an endoscopic surgical procedure. Some surgical instruments can have a housing or handle portion, an elongate shaft, and an end effector that can be selectively coupled to the elongate shaft. In certain aspects, the end effector can be "modular," i.e., selectively attached and detached from the shaft. While the modularity of the end effector can improve the device's versatility, it can be difficult to load an end effector onto a surgical device. In some instances, a loading device separate from the surgical instrument that operates the end effector is used to deliver end effectors to the surgical instrument. Certain loading devices are designed to have an articulating distal portion that holds the end effector in a fixed position during the loading process. However, the end effector and the distal portion of the loading device can undesirably move relative to the shaft of the surgical device onto which the end effector is loaded. Still further, during some surgical procedures it can be desirable to adjust an angle of the articulating distal portion of the loader relative to the loader's elongate shaft and/or the shaft of the instrument on which the end effector is being loading. Existing loading devices typically include cable or wire based articulation systems that tension the cable/wire to articulate the distal portion of the loader and these cable/wire based systems can cause undesirable relative motion between the end effector and the shaft of the surgical device on which the end effector is being loaded. This can make it difficult to attach the end effector onto the distal end of the surgical device and to withdraw the end effector from the loading device. In fact, in some instances, a user may think that the end effector was properly loaded, only to discover after the surgical device is moved away from the loader that the end effector and device were not properly aligned so the end effector was not properly secured to the device.

Accordingly, there is a need for articulating surgical devices and loaders having stabilizing features.

SUMMARY

End effector delivery devices are provided that include stabilizing features that facilitate loading an end effector onto a surgical device. In one exemplary embodiment, an end effector delivery device includes an elongate shaft having a lumen formed therein that extends along a length of the elongate shaft. An articulation rack can extend through at least a portion of the lumen of the elongate shaft, the articulation rack having teeth formed on it. The delivery device can have an articulating delivery end coupled to a distal end of the elongate shaft, the articulating delivery end having a hinge at which a distal portion of the articulating delivery end is configured to pivot with respect to a proximal portion of the articulating delivery end. The distal portion of the articulating delivery end can be configured to releasably hold an end effector. The delivery device can include a pinion having teeth meshed with the teeth of the articulation rack, the pinion being coupled to the hinge such that translation of the articulation rack along a longitudinal axis extending through the elongate shaft rotates the pinion to change an angle between the articulating delivery end and the elongate shaft.

The device can vary in any number of ways. For example, the device can include first and second deformable washers having a plurality of protrusions formed on an outer surface thereof that frictionally engage a plurality of recesses formed on inner, opposed surfaces of the proximal portion of the articulating delivery end. In some embodiments, each washer can include a plurality of protrusions spaced apart along an outer surface of each washer. The plurality of protrusions can be configured such that as the articulation rack is advanced, the plurality of protrusions deform and allow the first and second washers to rotate until the plurality of protrusions frictionally engage recesses of the plurality of recesses that are adjacent to the recesses in which the plurality of protrusions were previously engaged.

The deformable washers can have various features. Each washer can have an opening formed in it that defines an inner wall, the inner wall having a plurality of keys projecting from the inner wall. In some embodiments, the plurality of protrusions on the washers can be spaced apart along one hemisphere of the outer surface of each of the first and second washers such that the angle between the articulating delivery end and the elongate shaft has a maximum angle of 90 degrees with respect to the longitudinal axis extending through the elongate shaft. In some embodiments, the first and second washers can be formed from an elastic material.

The deformable washers can be disposed at various locations on the delivery device. For example, the first and second washers can be offset from the longitudinal axis extending through the elongate shaft. A shaft can extend through the pinion and through the first and second washers and can be configured so that rotating the pinion in a first direction also rotates the first and second washers in the first direction.

The end effector delivery device can include features that facilitate articulation of the delivery end relative to the elongate shaft. For example, one or more driving pinions can be coupled to a proximal end of a driving rack, the one or more driving pinions having teeth meshed with the teeth of the driving rack. Rotation of the one or more driving pinions can effect translation of the articulation rack along the longitudinal axis extending through the elongate shaft. The delivery device can further include a housing from which the elongate shaft extends, the housing having an actuator configured to translate the articulation rack along its longitudinal axis.

In another exemplary embodiment, an end effector delivery device includes an elongate shaft having proximal and distal ends and a central longitudinal axis. The device can include a hinge having a proximal portion, a distal portion, and a pivot at which the distal portion of the hinge pivots relative to the proximal portion of the hinge. The proximal portion of the hinge can have a proximal end coupled to the distal end of the elongate shaft and a distal end with first and second opposed arms. First and second deformable washers having a plurality of protrusions formed on the washers' outer surfaces can frictionally engage a plurality of recesses formed on inner surfaces of the first and second opposed arms. An end effector delivery end can be coupled to the distal portion of the hinge and can be configured to releasably hold an end effector. When the distal portion is being articulated, an angle between the end effector delivery end and the elongate shaft changes when at least some of the plurality of protrusions of the first and second deformable washers deform and move to different recesses of the plurality of recesses of the first and second opposed arms.

The deformable washers can have various features. For example, each washer can include an opening formed in it that defines an inner wall, the inner wall having a plurality of keys projecting from the inner wall and spaced radially along the inner wall. In some embodiments, the plurality of protrusions on the washers can be spaced apart along one hemisphere of the outer surface of each of the first and second deformable washers such that an angle formed between the proximal and distal portions of the hinge has a maximum angle of 90 degrees with respect to a longitudinal axis of the proximal portion of the hinge.

The delivery device can further include an articulation rack coupled to a toothed pinion, the toothed pinion being coupled to the pivot such that distal advancement of the articulation rack rotates the toothed pinion and the first and second washers about a central rotational axis of the pivot to adjust an angle between the proximal and distal portions of the hinge. The end effector delivery device can have an unarticulated position in which the distal portion of the hinge is coaxial with the elongate shaft. In some embodiments, when the distal portion of the hinge is in an articulated position, a frictional force applied by the first and second deformable washers to the distal portion of the hinge can be greater than the frictional force applied by the first and second deformable washers when the distal portion is in the unarticulated position.

An exemplary surgical method includes articulating a distal portion of a loading device having an end effector removably coupled to it relative to an elongate shaft of the loading device using a rack-and-pinion. An angle between the distal portion and the elongate shaft can be maintained by a biasing force applied by washers disposed in a hinge coupled between the elongate shaft and the distal portion of the loader. The surgical method can include loading the end effector onto a surgical device.

The method can vary in any number of ways. For example, the washers can include a plurality of deformable protrusions formed on an outer surface thereof that can apply the biasing force to the hinge. In some embodiments, a plurality of recesses formed in the hinge can be engaged by the deformable protrusions when the biasing force is applied, and the deformable protrusions can be configured to move to different recesses of the plurality of recesses as the angle between the distal portion and the elongate shaft is adjusted. The method can further include adjusting the angle formed between the distal portion and the elongate shaft by applying a force via the rack and pinion that is sufficient to overcome the biasing force applied by the washers.

BRIEF DESCRIPTION OF DRAWINGS

This disclosure will be more fully understood from the following detailed description taken in conjunction with the accompanying drawings, in which:

FIG. 6C is a perspective view of one deformable washer of FIG. 6B having a plurality of protrusions formed thereon;

FIG. 6D is a perspective detailed view of a proximal coupler of the hinge portion of FIG. 6B, the coupler having a plurality of recesses configured to receive the protrusions of the deformable washers of FIG. 6B;

FIG. 6E is a cross-sectional view of the coupler of FIG. 6A taken along the line E-E, the coupler being mated with a rod that holds the first and second deformable washers;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, to the extent features, sides, or steps are described as being "first" or "second," such numerical ordering is generally arbitrary, and thus such numbering can be interchangeable. Additionally, to the extent features are described as being "upper" or "lower," these terms are relative and are not meant to limit the orientation of the devices and their respective components.

Loading devices configured to load an end effector onto a surgical device are described. The devices generally include a housing having an actuator, an elongate shaft extending distally from the housing, and a distal articulating portion that can be positioned at various angles relative to the elongate shaft. The articulating distal portion of the loading device can also be configured to selectively couple to or otherwise hold an end effector to be loaded onto a surgical device. The loading devices can include features for stabilizing and holding the distal articulating portion at a particular angular position relative to the shaft. In some embodiments, these features can be disposed distal to the elongate shaft, such as part of a joint assembly. The joint assembly can include first and second deformable washers having protrusions that can seat in corresponding recesses formed in the joint assembly. The deformable washers can apply a biasing force that can hold the distal articulating portion in a desired angled position with respect to the elongate shaft of the loading device. This biasing force can also prevent the angle of the articulating distal portion from changing during a surgical procedure until a driving mechanism of the loader is engaged by a user. An internal drive mechanism can be operated to apply sufficient force to deform the washers and rotate the washers to the next rotational position to change the angle of the articulating distal portion relative to the elongate shaft of the loader. Further, the loading device can include features that indicate when the distal portion is articulated, and, optionally, the angle of the articulation.

Figure 1:
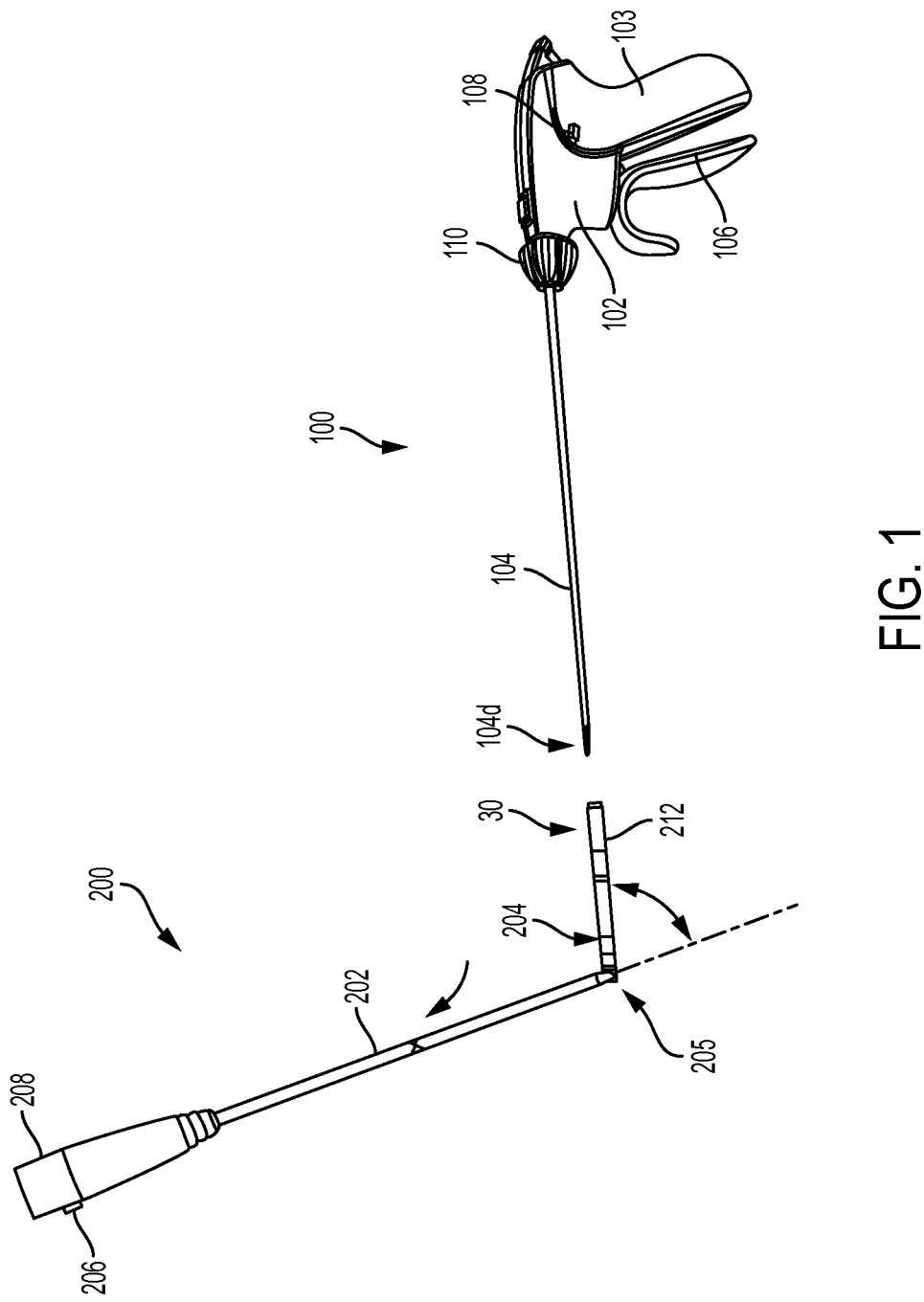
FIG. 1 is a perspective view of exemplary embodiments of a surgical device and a loading device prior to loading an end effector contained in the loading device onto the surgical device.

FIG. 1 shows an exemplary end effector loading/delivery device 200 that includes a housing or handle 208 and a shaft 202 extending distally therefrom. The loading device 200 has an articulating distal portion 204 (also referred to herein as a delivery end) controlled by one or more actuators, such as actuator 206. A pivot joint 205 can couple the articulating distal portion 204 to the shaft 202 and the tube 204 can be angulated relative to the shaft 202 by engaging actuator(s) on the housing 208. As will be discussed in greater detail below, the loader 200 can be configured to releasably hold an end effector 30 and to present the end effector 30 to a surgical instrument. In the illustrated embodiment, when the end effector 30 is coupled to the loading device 200, a tube 212 of an end effector 30 is positioned adjacent to the articulating distal portion 204 of the loading device 200.

FIG. 1 also shows an exemplary surgical instrument or device 100 that can couple to the end effector 30 disposed in the loader 200. The device 100 can have a housing or handle portion 102 and an outer elongate shaft 104 extending distally from the housing 102, the shaft 104 having a distal end 104d configured to have an end effector selectively coupled to it. The elongate shaft 104 can extend from a distal, upper portion of the housing 102. The housing 102 can include a closure actuator 106, such as a pivotable trigger, that is configured to move relative to the housing 102 and to a stationary handle 103 to actuate an end effector when an end effector is coupled to the shaft 104.

The surgical device 100 can include various components that facilitate use of the device during a surgical procedure. For example, the housing 102 can include a locking switch 108 that can be selectively activated to lock the closure actuator 106 in a fixed angular position relative to the housing 102. By way of further example, the housing 102 can include a knob 110 configured to rotate the elongate shaft 104 and thus an end effector coupled thereto. Still further, the device 100 can include both intermediate and inner shafts 128 and 138, respectively, (shown in FIG. 2B) disposed within the elongate shaft 104 and being configured to move proximally and distally relative to the elongate shaft 104. As will be described in greater detail below, both the intermediate and inner shafts 128, 138 can be used to assist in mating end effectors to the elongate shaft.

Figure 2A:
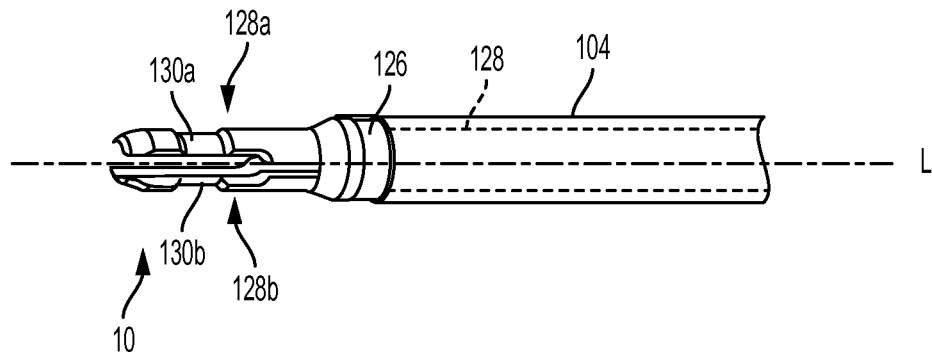
FIG. 2A is a side view of a distal mating feature of the elongate shaft of the surgical device of FIG. 1.
Figure 2B:
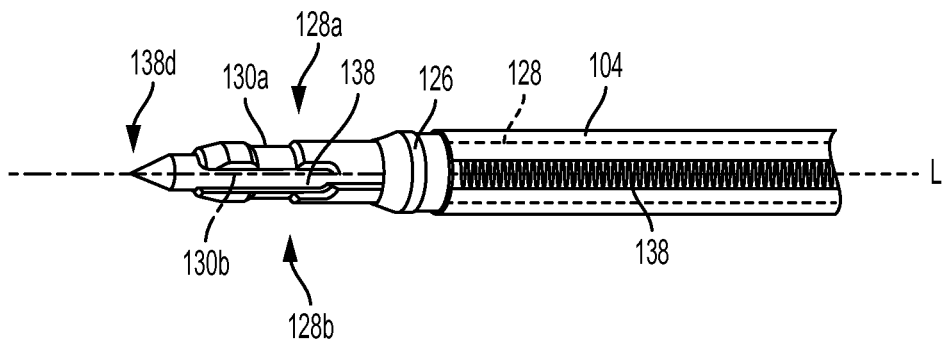
FIG. 2B is a side view of the distal mating feature of FIG. 2A having an obturator extending distally therethrough.

FIGS. 2A and 2B illustrate the distal end 104d of the shaft 104 in greater detail, including exemplary attachment mechanisms located at the distal end 104d of the elongate shaft 104 so that an end effector (not shown) can be mated to the shaft 104. The attachment mechanisms can form a loading zone 10 for loading an end effector. While the attachment mechanism can vary, in the illustrated embodiment a circumferential groove 126 can be positioned around an outer surface of a distal portion of the shaft 104. First and second arms 128a, 128b can project distally from the distal end 104d of the shaft 104 and can be coupled to or otherwise integrally formed on an intermediate shaft 128. The arms 128a, 128b can be axially slidable relative the elongate shaft 104 and can be resiliently deflectable medially into the gap. The arms 128a, 128b can each have a mating feature, which in this embodiment is a stepped lateral notch 130a, 130b.

A distal tip 138d of an inner shaft 138 (shown as a shaded region in FIG. 2B) can be positioned medially relative to the arms 128a, 128b and can be axially slidable relative to the arms 128a, 128b. More specifically, the distal tip 138d of the inner shaft 138 can slide between an unlocked position in which the distal tip 138d of the inner shaft 138 is proximal to the arms 128a, 128b, i.e., proximal of the loading zone 10, allowing medial deflection of the arms 128a, 128b (as shown in FIG. 2A), and a locked position in which the distal tip 138d of the inner shaft 138 is aligned with or distal to the arms 128a, 128b, i.e., aligned with or distal of the loading zone 10, and to prevent medial deflection of the arms 128a, 128b (as shown in FIG. 2B). In certain aspects, the inner shaft 138 and the arms 128a, 128b can slide independently along a longitudinal axis L of the elongate shaft 104. As shown in the embodiment of FIG. 2B, the distal tip 138*d* of the inner shaft 138 is also referred to herein as an obturator tip which can be pointed and/or sharpened such that the distal tip 138*d* can pierce through tissue. In the illustrated embodiment, the distal ends of the arms 128*a*, 128*b* and the distal end 104*d* of the elongate shaft 104 can taper from a proximal-to-distal direction and this can facilitate passing the arms 128*a*, 138*b* and the elongate shaft 104 through an incision (not shown), such as an incision formed by the distal tip 138*d*. As will be appreciated by persons skilled in the art, the distal tip 138*d* of the intermediate shaft need not be sharpened or pointed and the outer and intermediate shafts can include various types of attachment mechanisms for mating with an end effector and need not include a taper, grooves, etc.

Figure 3A:
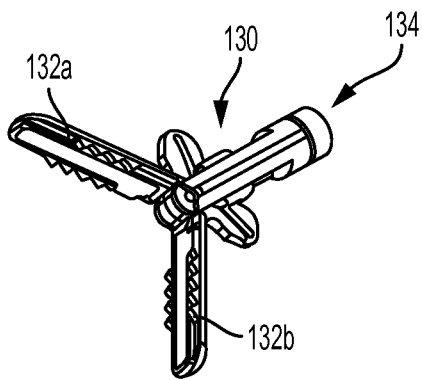
FIGS. 3A-3D are perspective view of various end effectors that can be coupled to the elongate shaft of the surgical device of FIG. 1.
Figure 3B:
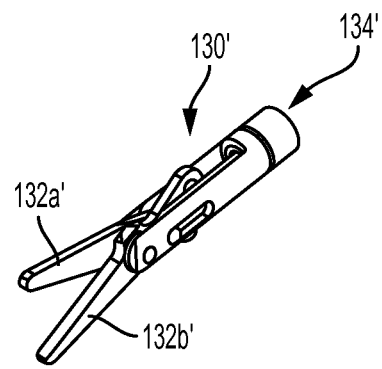
Figure 3C:
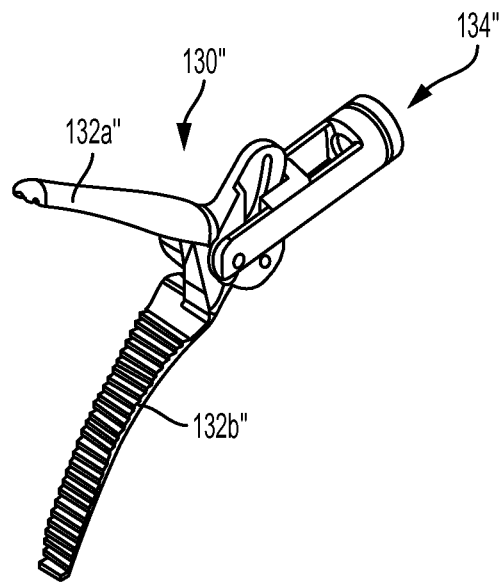
Figure 3D:
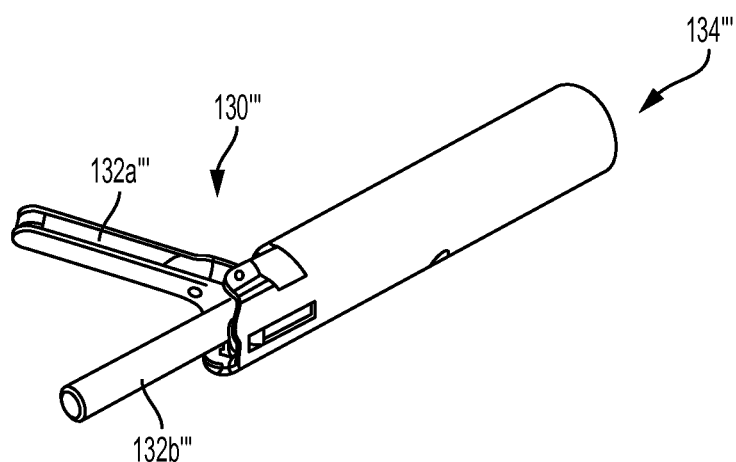

FIGS. 3A-3D provide non-limiting examples of end effectors that can be attached to the instrument 100. All or some of the end effectors can be provided in a kit so a surgeon can interchange the end effectors as needed for a particular surgical procedure. FIG. 3A illustrates a bi-polar jawed end effector 130 having first and second jaws 132*a*, 132*b*, FIG. 3B illustrates a cutting shears end effector 130' having first and second jaws 132*a'*, 132*b'*, FIG. 3C illustrates a Maryland dissector end 130" effector having first and second jaws 132*a"*, 132*b"*, and FIG. 3D illustrates an ultrasonic shears end effector 130''' having first and second jaws 132*a'''*, 132*b'''*. Each of the end effectors 130, 130', 130", and 130''' can have a proximal opening formed 134, 134', 134", 134''' therein that can be configured to mate with attachment mechanisms of the intermediate shaft and the outer shaft. For example, the openings 134, 134', 134", and 134''' can be sized and shaped to extend over the first and second arms 128*a*, 128*b* of FIGS. 2A and 2B. While the illustrated end effectors 130, 130', 130", and 130''' have cooperating jaws; the end effectors 130, 130', 130", and 130''' need not include jaws and/or the effectors could also include hook knives, snares, and the like. As will be appreciated, any of the end effectors 130, 130', 130", and 130''' can also be configured to transmit energy to tissue and in these embodiments the housing and the shaft of the surgical instrument can have appropriate energy transmission mechanisms. For example, appropriate electrical connections can be added to the bi-polar jawed end effector 130' of FIG. 3A and can extend through the elongate shaft 104. Similarly, an ultrasonic transducer and waveguide can be added to the ultrasonic shears end effector 130''' of FIG. 3D.

End effectors such as those illustrated in FIGS. 3A-3D can be mated to the elongate shaft 104 in a variety of ways. For example, a proximal end of the end effector can be positioned adjacent to the distal end of the elongate shaft and the inner and/or intermediate shafts can be manipulated to hold the end effector in a fixed position on the elongate shaft 104 and to allow a user to open and close jaws of the end effector by operating the closure actuator 106. U.S. Patent Application Publication No. 2011/0087267 entitled "Method for Exchanging End Effectors in Vivo," and U.S. patent application Ser. No. 14/836,069 entitled "Surgical Device Having Actuator Biasing and Locking Features" and filed on Aug. 26, 2015, are incorporated by reference herein in their entirety and provide other exemplary end effectors that can be mated to the surgical device 100, and ways by which end effectors can be mated to a surgical device. By way of non-limiting example, in some embodiments, an end effector can be coupled to a coupling (not shown, by described in greater detail in the above-referenced patent application disclosures) at one end of the coupling, and the other end of the coupling can be attached to the elongate shaft 104 such that the coupling is an intermediary piece that couples the end effector to the surgical device 100.

Figure 4:
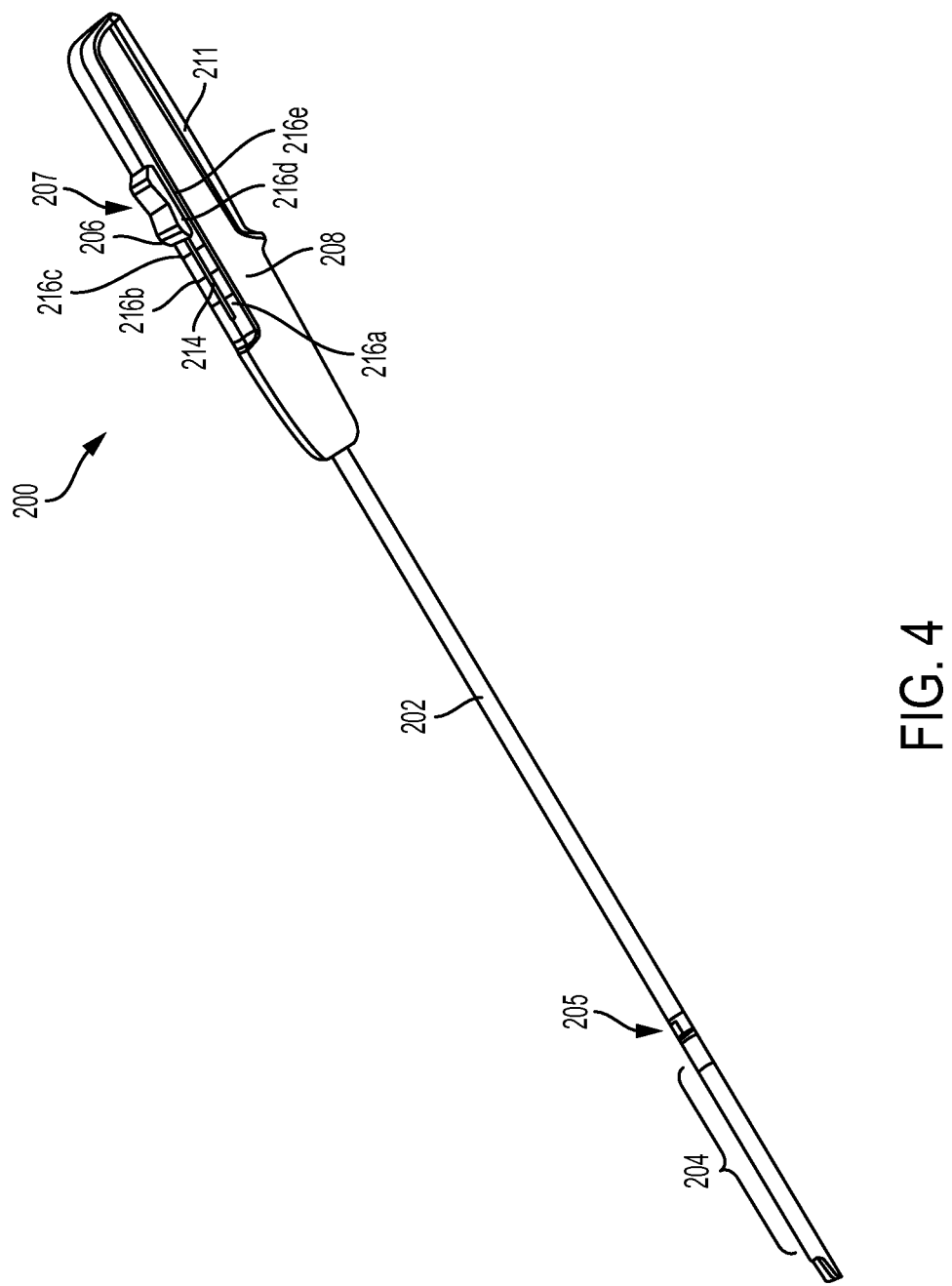
FIG. 4 is a perspective view of the loading device of FIG. 1 which can be used to load an end effector onto the surgical device of FIG. 1.

The loading device 200 of FIG. 1 is shown in greater detail in FIG. 4. The loader 200 can have a rigid and substantially straight outer shaft 202 as shown, or the shaft 202 can be curved and/or flexible, which would be beneficial for introducing the shaft 202 into a natural orifice. The articulating distal portion or delivery end 204 can be controlled by one or more actuators, such as the slider 206 disposed on the handle 208 of the loader 200. As will be appreciated, the distal portion 204 can be articulated prior to or after it is inserted into a surgical site. The pivot joint 205 can couple the articulating distal portion 204 to the shaft 202. The distal portion 204 can be angulated relative to the shaft 202 by engaging the slider 206 and moving the slider 206 relative to the housing 208.

As previously mentioned, the loader 200 can be configured to hold an end effector (not shown) therein and to present the end effector for loading onto the shaft 104 of the instrument 100 of FIG. 1. As will be appreciated, any end effector can be used including the end effectors shown in FIGS. 3A-3D. The distal portion 204 can include one or more engagement features (not shown) for holding an end effector (not shown) therein. While the engagement feature may vary, in an exemplary embodiment a plurality of leaf springs (not shown) can be disposed within the distal portion 204 and can provide an interference fit with an end effector to frictionally hold the end effector in the distal portion 204 of the loader 200. In the illustrated embodiment, when an end effector is loaded in the distal portion 204, a distal end of the end effector is positioned closest to the pivot joint 205. This arrangement prevents the jaws (not shown) of the end effector from opening when the end effector is positioned within the distal portion 204 of the loader 200.

The housing 208 of the loading device 200 can have various configurations. For example, the housing 208 can include one or more recesses and/or can be contoured along a proximal, lower surface 211 thereof to facilitate being grasped by a user's hand. The actuator/slider 206 can also be contoured along outer surface thereof or can include a recess or depression 207 having one or more surface features that facilitate friction between a user's fingers and/or thumb and the slider 206. An elongate track 214 can be formed on a central, upper surface of the housing 208 and the slider 206 can move proximally and distally along the track 214. As shown in FIG. 4, the track 214 can include a plurality of markings spaced at equal distances apart along the track 214, such as five markings 216*a*, 216*b*, 216*c*, 216*d*, 216*e*. Though not shown, each of the markings 216*a*, 216*b*, 216*c*, 216*d*, 216*e* can be labeled to assist a user with monitoring a degree of articulation of the articulating distal portion 204 relative to the elongate shaft 202. For example, proximal marking 216*e* can be labeled 0 degrees and second marking 216*d* that is adjacent and distal to the proximal marking 216*e* can be labeled 30 degrees. For another example, in loading devices where the articulating distal portion is configured to be angled in two different directions relative to the elongate shaft, a central marking (such as the marking 216*c*) can be labeled 0 degrees to indicate that the distal portion is axially aligned with the elongate shaft. In some embodiments, the proximal markings can be labeled with positive angles and the distal markings can be labeled with negative angles to reflect both the degree of articulation of the distal portion as well as the direction of articulation. As will be appreciated, the number of markings, the particular spacing between the markings, and the degree of articulation of the distal portion 204 relative to the shaft 202 can vary but can be generally selected so that the when a distal end 206d of the slider 206 is positioned adjacent to one marking, the marking corresponds to and accurately informs a user as to the degree of articulation of the distal portion 204.

Figure 5A:
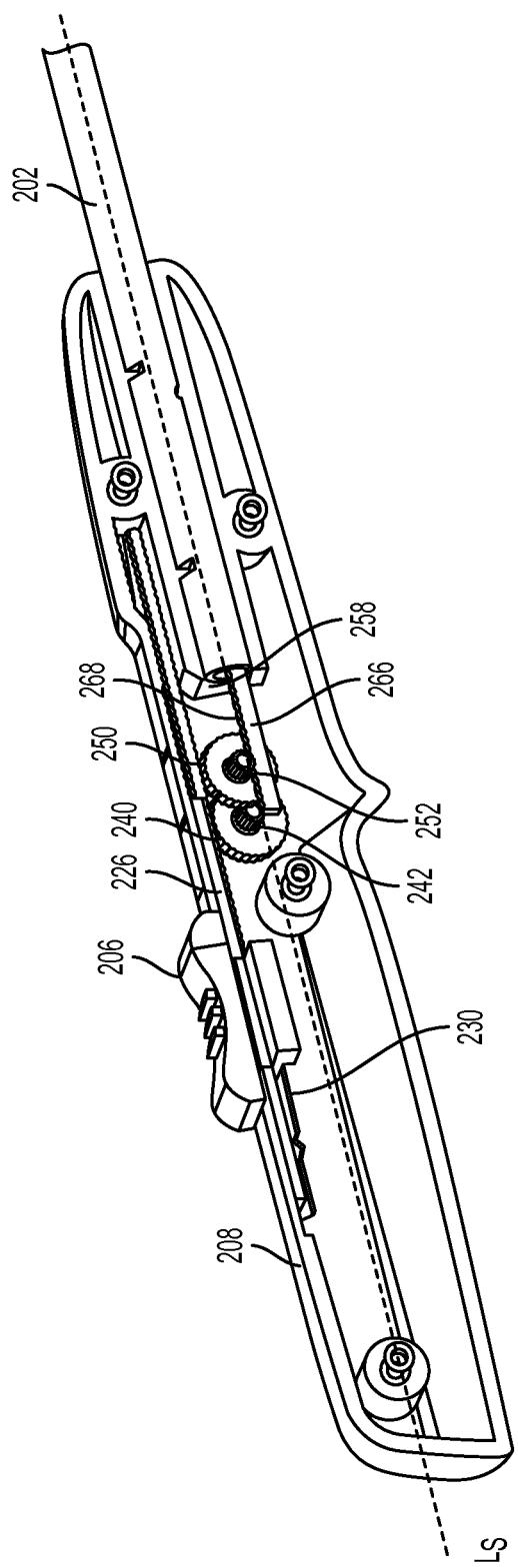
FIG. 5A is a perspective view of internal actuation components of the loading device of FIG. 4.
Figure 5B:
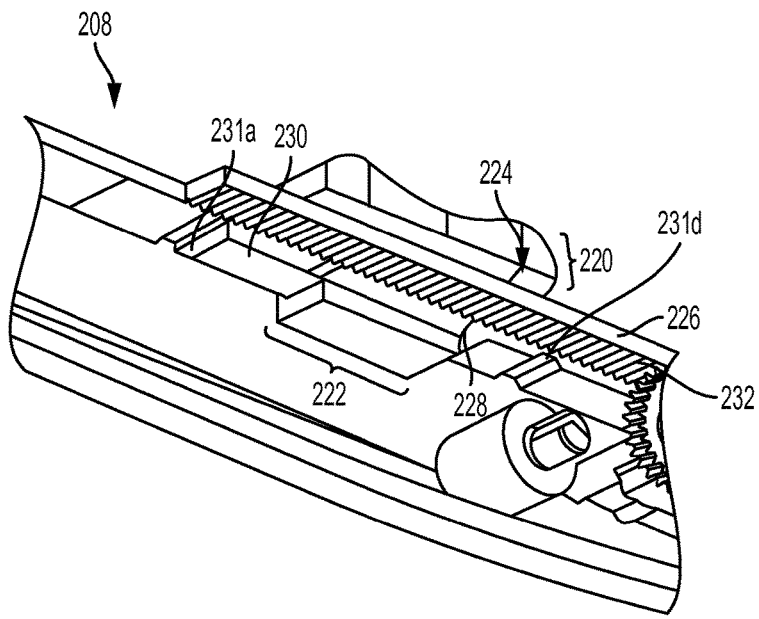
FIG. 5B is a semi-transparent, detailed perspective view of some of the articulation control components of FIG. 5A.
Figure 5C:
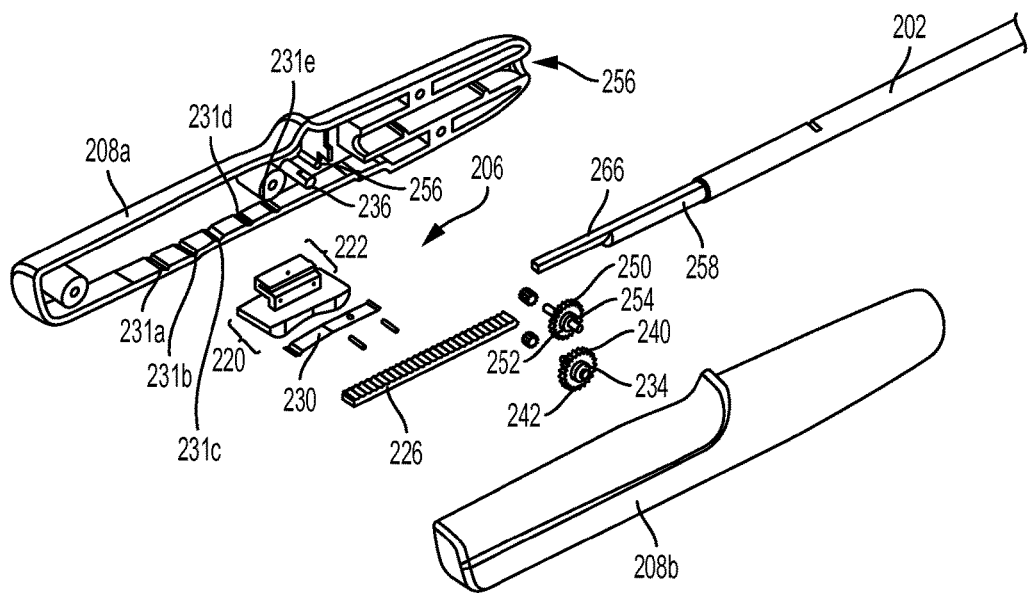
FIG. 5C is an exploded view of the internal actuation components of the loading device of FIG. 5A.

FIGS. 5A-5C illustrate the housing 208 of the loading device 200 in greater detail. Beginning with the actuator slider 206, the actuator slider 206 can have an external portion 220 that can be positioned outside of and external to the housing 208 and directly contacted by a user. An internal portion 222 of the slider 206 can mate with various internal actuation components. For example, the internal portion 222 of the slider 206 can have a first lateral recess 224 that can receive an actuator rack 226 therebetween and a second lateral recess 228 that can engage a slider detent spring 230 that can engage with one or more recesses, such as engaging with two detents 231a, 231d to frictionally hold the slider 206 in its current position even as the distal portion 204 (not shown) of the loader 200 is being articulated. Detents 231a, 231b, 231c, 231d, 231e are shown in FIG. 5C, though there can be any number of detents formed in the housing 208. These recesses or detents can also provide tactile and/or audible feedback to a user to indicate that the slider 206 is locked relative to the track 214. The locking of the slider 206 relative to the track 214 permits incremental articulation of the distal portion 204 relative to the elongate shaft 202 and can also prevent back drive of the distal articulation portion 204 that might otherwise occur when forces are applied to the distal portion 204 during a surgical procedure. The actuator rack 226 can be disposed in the housing 208 and can have a rectangular cross-sectional shape with teeth 232 formed on at least one of its outer surfaces. As shown in FIG. 5B, when the actuator rack 226 is received in the first lateral recess 224 of the slider 206, the teeth 232 can be oriented toward the lower surface of the housing 208. The slider 206 and the actuator rack 226 can move together as a unit such that moving the slider 206 proximally/distally along the track 214 causes the actuator rack 226 to move in the same direction.

The actuator rack 226 can interact with other actuation components to facilitate articulation of the distal portion 204 of the loader 200. As shown in FIG. 5A, a first drive gear 240 can be disposed in the housing 208, can mesh with the actuator rack 226, and can rotate about a first gear shaft 234. The first gear shaft 234 can be received in and can rotate relative to a first shaft recess 236 formed in the housing 208. The first drive gear 240 can be laterally offset from a central longitudinal axis $L_S$ extending through the housing 208 and through the elongate shaft 202 of the loader 200. A first pinion 242 can rotate along with the first drive gear 240 on the first gear shaft 234 and can also be laterally offset from the central longitudinal axis $L_S$. The first pinion 242 can mesh with a second drive gear 250 disposed on a second gear shaft 254, the second gear shaft 254 being received in and configured to rotate relative to a second shaft recess 256 formed in the housing 208. A second pinion 252 can be disposed on the second gear shaft 254 and the second pinion 252 can rotate with the second drive gear 250. The second pinion 252 can be axially aligned with the central longitudinal axis $L_S$ and can mesh with teeth 268 formed on the driving rack 266 such that rotational motion of the pinion 252 causes the rack 266 to advance linearly in a proximal or distal direction. The first and second drive gears 240, 250 can have the same diameter and number of teeth or in other aspects can have different diameters and/or number of teeth such that the rotation is mechanically advantaged. As will be appreciated, the particular gear mechanisms in the housing 208 can vary.

As shown in FIG. 5C, the housing 208 can include first and second portions 208a, 208b that can be selectively detached from one another to reveal the internal actuation components. Such a configuration is also conducive to fixing, cleaning, or replacing components disposed in the housing 208, or for doing the same to the housing 208 itself. FIG. 5C also illustrates the outer elongate shaft 202 of the loading device 200, which can be received in an elongate opening 256 formed in the housing 208, the opening 256 extending along the central longitudinal axis $L_S$. A rack guide 258 can be disposed within the elongate shaft 202 and can extend distally from the housing/handle portion 208. The rack guide 258 can have a substantially elongate cylindrical shape that allows the rack guide 258 to be disposed within and remain fixed relative to the elongate shaft 202. The rack guide 258 can have a recess formed thereon, such as a rectangular shaped cutout formed along a longitudinal length thereof, sized and shaped to receive the driving rack 266. The driving rack 266 can have teeth (not shown) formed on a first lateral surface. The driving rack 266 can be longer than the elongate shaft 202 such that the driving rack 266 can extend between and move relative to the elongate shaft 202 and the housing 208 to articulate the articulating distal portion 204 (not shown).

FIGS. 6A-6F illustrate components of the pivot joint or hinge 205 and their interaction with the driving rack 266 that extends from the housing 208. A distal portion 266d of the driving rack 266 can have the teeth 268 disposed on a surface that faces toward the slider 206 (not shown) and faces toward an upper surface of the housing 208 (not shown). As will be appreciated, the driving rack 266 can couple from the housing 208 to the pivot joint 205 or one or more intermediate rods or racks can extend through the elongate shaft 202 and operably couple the driving rack 266 to the internal actuation components of the housing 208. The distal portion 266d of the rack 266 can be received in an elongate opening 267 formed in a coupler 270 that forms a proximal portion 205p of the pivot joint 205. The coupler 270 can have a proximal end 270p and a distal end 270d, the proximal end 270p of the coupler 270 mating with the distal end 202d of the elongate outer shaft 202. The distal end 270d of the coupler 270 can have first and second arm portions 272, 274 defining a substantially U-shaped space 276 therebetween for receiving articulation mechanisms that allow the distal portion 204 to pivot about the pivot joint 205 and hold the distal portion 204 in an articulated position. For example, the articulation mechanisms can include a modified spur gear 278 (which can also be referred to as a modified pinion 278) having teeth 280 formed around a first portion of its outer circumference and having substantially planar surface 282 formed around a remaining portion of the outer circumference of the gear 278. The teeth 280 of the spur gear 278 can be spaced apart along about 50% to about 75% of the circumference of the gear 278, although other configurations including those in which the teeth are formed along the entire circumference of the gear 278 are possible.

Figure 6A:
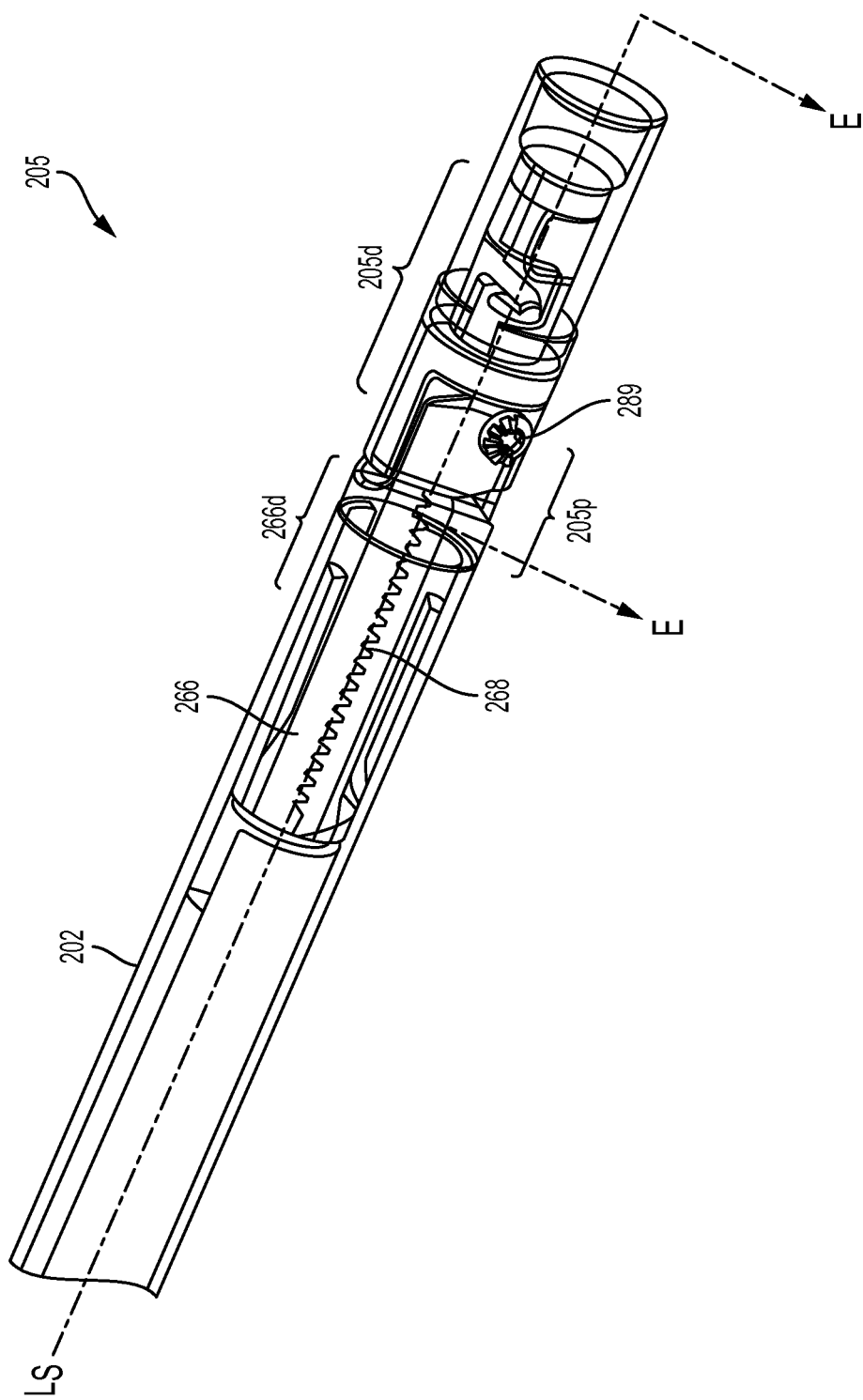
FIG. 6A is a perspective view of a hinge portion of the loading device of FIG. 4.
Figure 6B:
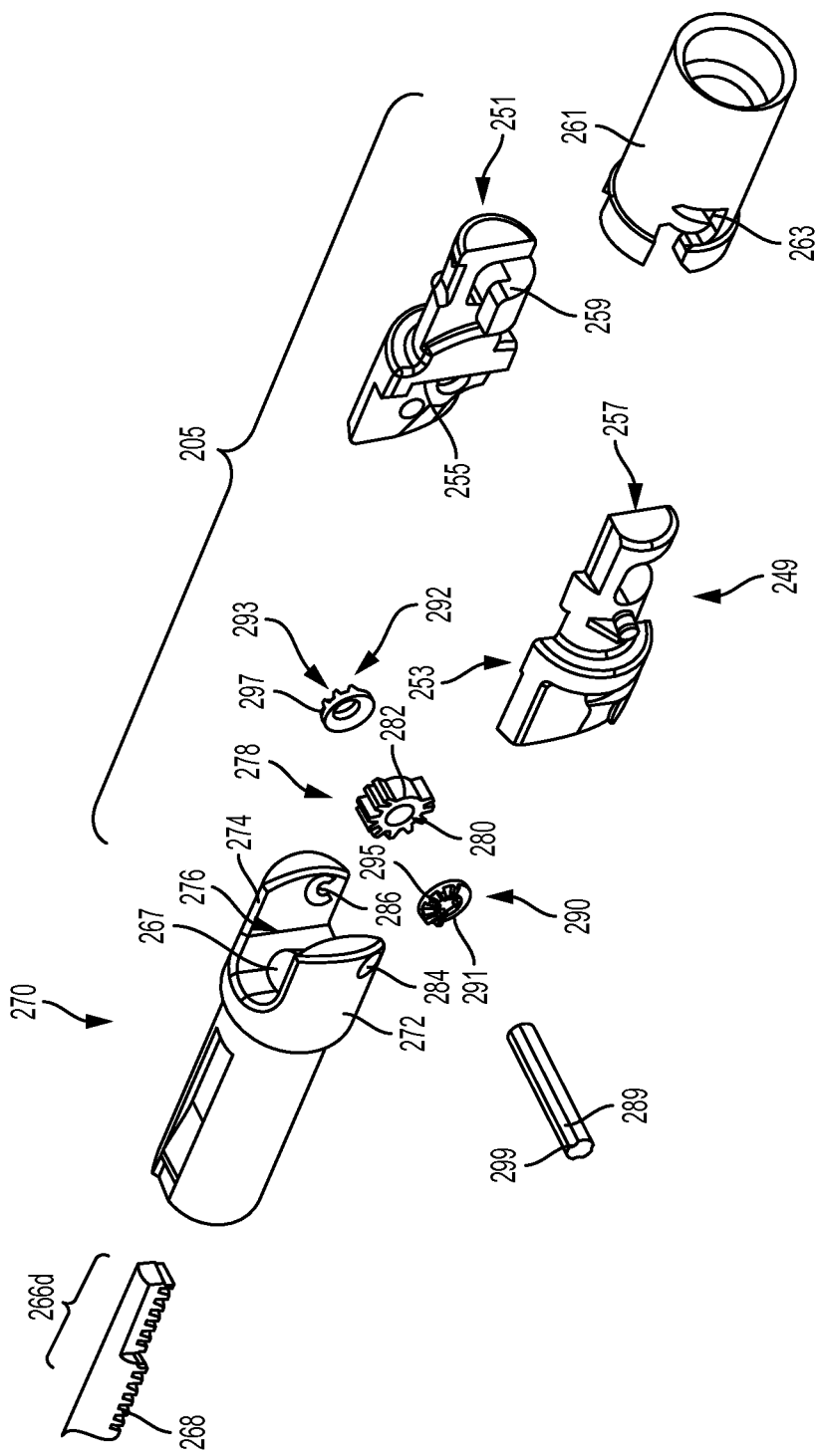
FIG. 6B is an exploded view of the hinge portion of FIG. 6A illustrating various stabilization components such as a rotatable gear, first and second deformable washers, and an articulation rack.

The pivot joint 205 can include first and second deformable washers 290, 292, as shown in FIGS. 6B and 6C, and the washers 290, 292 can act as secondary holding features to the spur gear 278 to hold the loader 200 in an articulated position. The washers 290, 292 can each have central openings 291, 293 extending therethrough. A plurality of protrusions 295, 297 can be formed around and spaced along a first hemisphere of an outer face each of the washers 290, 292 and a second hemisphere of the outer face of each of the washers 290, 292 can be substantially planar and smooth, lacking any protrusions. As shown in FIG. 6C, the first washer 290 can include the protrusions 295 spaced apart by planar portions 279, which can be on the same plane as the second hemisphere of the washer 290. The protrusions 295, 297 can have a substantially triangular cross-sectional shape, as shown, or can be shaped in various other ways. The protrusions 295, 297 can be equal to or slightly larger in size than the plurality of recesses formed in the arm portions 272, 274 of the coupler 270 (such as the plurality of recesses 285a, 285b, 285c, 285d, 285e, 285f shown in FIG. 6D) so that the protrusions 295, 297 of the respective washers 290, 292 frictionally engage with the respective recesses and apply a biasing force that holds the washers 290, 292 in position relative to the arm portions 272, 274. As also shown in FIG. 6C, the protrusions 295, 297 can have a longitudinal height at an outer circumference of the respective washer that is greater than a longitudinal height at an inner circumference of the washer such that the protrusions are cone-shaped, and this can result in an increased biasing force than if the protrusions had a symmetrical shape. As will be explained in greater detail below, the arrangement of the plurality of protrusions 295, 297 on only one hemisphere of each of the washers 290, 292 in the illustrated embodiment can permit 90 degrees of articulation of the articulating distal portion 204 relative to the elongate shaft 202 of the loader 200.

The washers 290, 292 can be formed from various different materials configured to allow the respective protrusions 295, 297 to deform. For example, the washers 290, 292 can be formed from an elastic material and can include one or more elastomers. Exemplary materials used to form the washers 290, 292 include, by way of non-limiting example, ISOPLAST®, Isoprene, and Santoprene.

Referring back to the coupler 270 shown in FIG. 6B, an opening 284, 286 can be formed in each of the first and second arm portions 272, 274 of the coupler 270, respectively, and can extend through inner and outer surfaces of the arm portions 272, 274. The openings 284, 286 can be formed on a lower portion of the arm portions 272, 274 that is below the central longitudinal axis $L_S$, which also extends centrally through the coupler 270 such that the openings 284, 286 are offset from the central longitudinal axis $L_S$. The openings 284, 286 can be substantially circular-shaped or can be shaped in other ways known to those skilled in the art. A plurality of recesses can be formed on the inner surface of the first and second arm portions 272, 274 around an entire circumference of each of the openings 284, 286 or around a portion of the circumference of the openings 284, 286. For example, FIG. 6D shows the first arm portion 272 having a plurality of recesses 285a, 285b, 285c, 285d, 285e, 285f sized, shaped, and configured to receive the protrusions of the first washer. The second arm portion 274 can have identical plurality of recesses as the first arm portion 272 (the plurality of recesses on the second arm portion 274 are not visible in FIG. 6D). The plurality of recesses on the second arm portion 274 can mate with the protrusions of the second washer. The plurality of recesses can be formed on a lower portion of the coupler 270. There can be the same number of recesses as the number of protrusions formed on each of the washers 290, 292 or there can be a larger number of recesses than the number of protrusions. In embodiments where there a larger number of recesses, this can allow the respective washer 290, 292 to hold the articulating distal portion at an angle with a biasing force that is the same as when the washer 290, 292 is in its first, resting position in which the distal articulating portion 204 is axially aligned with the elongate shaft 202 of the loader 200. In other embodiments, the first and second arm portions 272, 274 of the coupler 270 need not include the plurality of recesses and instead the protrusions 295, 297 of the washers 290, 292 can engage directly with other surface features formed on the arm portions 272, 274 and/or with a relatively smooth surface of the arm portions 272,274, with enough friction being generated between the protrusions 295, 297 and the surface and/or surface features of the arm portions 272, 274 to maintain a desired location of the articulating distal portion 204 with respect to the elongate shaft 202. The recesses can also give a user tactile feedback as to when the protrusions 295, 297 of the washers 290, 292 engage with one or more of the recesses at the next rotational position.

The washers 290, 292 and the spur gear 278 can be positioned between the first and second arm portions 272, 274 of the coupler 270 as shown in FIG. 6E. Their respective central openings can be axially aligned with the openings 284, 286 formed in the arm portions 272, 274 and the spur gear 278 can be positioned between the first and second washers 290, 292. A rod or pin 289 can be inserted through the opening 284 in the first arm portion 272, through the central openings of the first and second washers 290, 292 and the spur gear 278, and through the opening 286 in the second arm portion 274. The rod 289 can thus mate these articulation components to the coupler 270 and serve as the pivot of the pivot joint 205. As best shown in FIG. 6A, the rod 289 and the washers 290, 292 can be offset from and positioned below the central longitudinal axis $L_S$. The rod 289 can include a plurality of keys 299 formed along an outer surface thereof that can mate with corresponding recesses formed on an inner wall of each of the washers 290, 292 (FIG. 6C illustrating planar portions 283 and protrusions 281 on the inner wall of the opening 291 of the washer 290) so that rotating the rod 289 causes corresponding rotation of each of the washers 290, 292.

As shown in FIGS. 6A and 6B, a distal portion 205d of the pivot joint 205 can include first and second pivotable hinge portions that can pivot as the spur gear 278 and the deformable washers 290, 292 are rotated. For example, a first hinge portion 249 and a second hinge portion 251 can be detachable and can have a substantially cylindrical shape when positioned in a side-by-side relationship. The first and second hinge portions 249, 251 can be received in the space 276 between the first and second arm portions 272, 274 of the coupler 270. The first and second hinge portions 249, 251 can each have lateral planar surfaces 253, 255 formed therein configured to receive the driving rack 266. Each of the first and second hinge portions 249, 251 can have an opening (not shown) formed in a proximal portion thereof and extending through and being perpendicular to outer and inner surfaces of the respective hinge portion. The openings can be configured to engage one of the first and second washers 290, 292 in a fixed mating relationship with the respective hinge portion 249, 251 such that rotation of the washers 290, 292 causes corresponding pivoting of the hinge portions 249, 251 relative to the coupler 270.

The first and second hinge portions 249, 251 can be configured to mate with various components to form the articulating distal portion 204. In the illustrated embodiment, a distal portion of each of the first and second hinge portions 249, 251 can each have a protrusion 257, 259 configured to mate with a corresponding slot formed on the distal end of an end effector (not shown). In the illustrated embodiment, the protrusion 257, 259 of the hinge portions 249, 251 mate with a tube 261 having two L-shaped slots (a first slot 263 shown in FIG. 6A and a second slot in the hinge portion 249 hidden from view) to form a bayonet connection. As will be appreciated, various other types of mating features can be used to couple the hinge portions 249, 251 to the tube 261, such as snap connections, threaded connections, and the like. In the illustrated embodiment, the tube 261 can couple to an end effector (not shown) and the tube 261 and the end effector can form the distal articulating portion 204 of the loader 200.

Figure 6F:
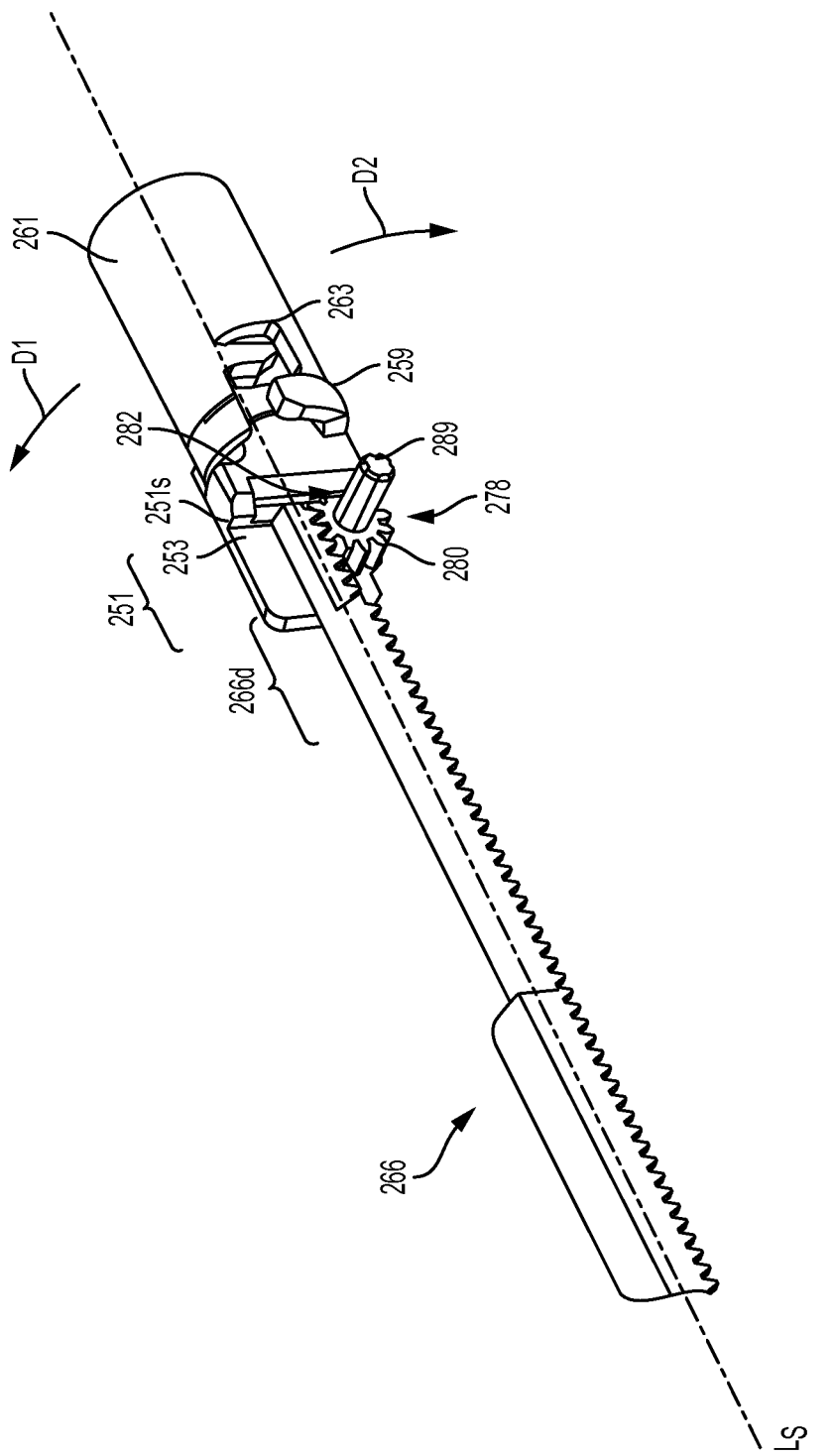
FIG. 6F is a perspective, partial view of the hinge portion of FIG. 6B including the articulation rack engaged with the rotatable gear.

FIG. 6F shows portions of the articulation mechanisms including the driving rack 266, the second hinge portion 251, and the tube 261 (the elongate shaft 202, the coupler 270, and the first hinge portion 249 of the loader 200 being hidden from view). The distal portion 266d of the driving rack 266 can mesh with the teeth 280 of the spur gear 278. The planar surface 282 of the spur gear 278 can contact a stop 251s formed in the second hinge portion 251, the stop 251s being defined along a distal surface of the recess 253 of the second hinge portion 251. The first hinge portion 249 can include a corresponding stop (not shown). This arrangement can allow proximal/distal movement of the driving rack 266 to rotate the spur gear 278 via the teeth 268 of the driving rack 266 engaging and meshing with the teeth 280 of the spur gear 278. Rotation of the spur gear 278 can cause corresponding rotation of the hinge portions 249, 251 because of the stops in the hinge portions 249, 251 contacting the planar surface 282 of the spur gear 278. Proximal movement of the driving rack 266 can rotate the spur gear 278 in a counter clockwise direction $D_1$ and distal movement of the driving rack 266 can rotate the spur gear 278 in a clockwise direction $D_2$ relative to the longitudinal axis $L_S$. This can cause corresponding rotation of the first and second washers 290, 292. Because the first and second washers 290, 292 are fixed relative to the first and second hinge portions 249, 251, the rotation of the washers can cause the first and second hinge portions 249, 251 to pivot in the direction of rotation relative to the elongate shaft 202. The tube 261 can be coupled to and positioned distal to the second hinge portion 251 via the slot 263 that receives the protrusion 259 of the second hinge portion 251. The tube 261 can also pivot along with the first and second hinge portions 259, 261 due to this fixed mating relationship.

Figure 7A:
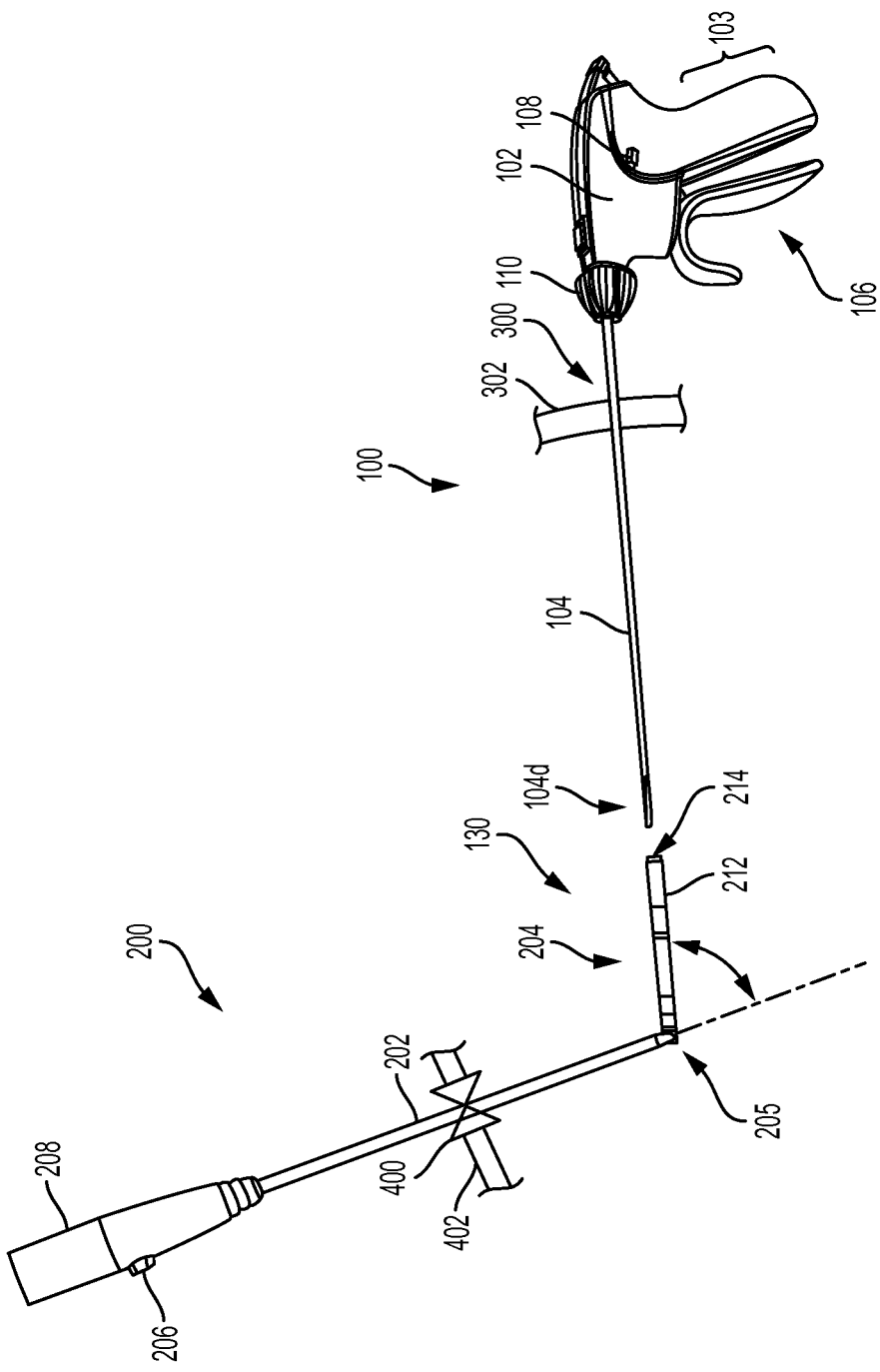
FIG. 7A is a perspective view of a delivery end of the loading device of FIG. 1 being positioned adjacent to and axially aligned with an elongate shaft of the surgical device of FIG. 1.

A method for performing a surgical procedure can include passing the elongate shaft 104 of the surgical instrument 100 through a first incision 300 as shown in FIG. 7A. The first incision 300 can be a percutaneous incision formed at least partially by a puncture formed with the distal obturator tip of the inner shaft (not shown) or the incision can be formed using a separate instrument. As the elongate shaft 104 passes through the incision 300 in a tissue wall 302. An end effector can be selected from a plurality of end effectors provided in a kit (though the description below refers to the end effector 130, any end effector can be used) and the loading process can begin as in FIG. 7A. The end effector 130 can be loaded ex vivo into the distal end of the loader 200. In this example, the end effector 130 has tissue grasping jaws, but as previously mentioned a variety of other end effectors could also be used. The distal end of the loader 200 with the end effector 130 loaded therein can be passed through a second incision 400 formed in a tissue wall 402 as shown. The second incision 400 can also be percutaneous incision spaced from the first incision 300. If pneumoperitoneum is desired, the incisions 300, 400 can have instrument seals such as by positioning a trocar in each incision and inserting the surgical instrument 100 or loader 200 through the trocar. In other embodiments, trocars need not be used and instead the resilience of the tissue can form a seal around the shaft 104, 202 of the instrument 100, 200 without the aid of a separate trocar or sealing device.

The tissue wall anatomies will vary based on the surgical procedure, but some non-limiting examples include percutaneous incisions extending into the abdomen, thorax, or pelvis. The incisions 300, 400 can be formed with a cutting or puncturing instrument and will typically be spaced apart from one another. The tissue walls 302, 402 can be the same or different anatomies. For example, tissue walls 302, 402 can both be the abdominal wall. In another example, the tissue wall could be an organ (e.g., stomach, colon, esophagus, etc.) accessed through a natural orifice, while the incision in tissue wall can be percutaneous. In yet another example, the first incision 300 can provide access to the abdomen, while the second incision 400 can provide access to the pelvis. The surgical end effector 130 can be selectively attachable in vivo and detachable in vivo to the attachment mechanism/loading zone located at the distal end of the elongate shaft 104 of the instrument 100. For in vivo attachment, the loader 200 can hold the end effector 130 during attachment to and detachment from the surgical instrument 100.

The distal portion 204 of the loader 200 is typically introduced and removed through an incision in-line with the shaft 202 and then articulated about the joint 205 in vivo to align the end effector 130 with the shaft 104 of the surgical instrument 100. In another embodiment, the end effector 130 can be loaded ex vivo onto the distal end 104d of the shaft 104 and then introduced into the surgical field through the first incision 300. In both examples, one or more engagement features 217 can hold a distal end (not shown) of the end effector 130 in a fixed position relative to the articulating distal portion 204 even as the distal portion 204 is angulated relative to the elongate shaft 202 of the loader 200.

To articulate the distal portion 204 of the loader 200, a user can engage the actuator 206 on the housing 208 of the loading device 200 and can move the actuator 206 proximally or distally along the track 214 until the slider detent spring 230 engages with one or more recesses (such as engaging two of the detents 231a, 231b, 231c, 231d, 231e formed on an inner surface of the housing 208). The detent spring 230 engaging with the detents can frictionally hold the slider 206 in its current position. Movement of the slider 206 in this first direction can cause corresponding movement of the actuator rack 226 in the same, first direction. For example, distal movement of the slider 206 and of the actuator rack 226 can rotate the first gear 240 and the first pinion 242 in a clockwise direction and can cause the second gear 250 and the second pinion 252 to rotate in a counter clockwise direction. Because the second pinion 252 contacts the teeth 268 of the driving rack 266, counter clockwise rotation of the second pinion 252 will drive the driving rack 266 distally.

Distal translation of the driving rack 266 can rotate the spur gear 278 in a clockwise direction. The planar surface 282 of the spur gear 278 can remain in contact with the stops on each of the first and second hinge portions 249, 251 (such as the stop 251s shown in FIG. 6E). The force from the driving rack 266 and the contact between the spur gear 278 and the hinge portions 249, 251 can eventually cause the protrusions 295, 297 on the washer 290, 292 to deform, allowing the washers 290, 292 to rotate in a counter clockwise direction and the protrusions 295, 297 to seat in the recesses formed in the coupler 270 at the next rotational position. This can cause the hinge portions 249, 251 and the articulating distal portion 204 to pivot about the pivot joint 205 in the clockwise direction $D_2$, as shown in FIG. 6E.

Likewise, translation of the slider 206 along the track 214 can cause the hinge portions 249, 251 and the articulating distal portion 204 to pivot in the direction $D_1$ as in FIG. 6E. More specifically, proximal movement of the slider 206 can cause the first gear 240 and the first pinion 242 to rotate in a counter clockwise direction. This can cause the second gear 250 and the second pinion 252 to rotate in a clockwise direction and the second pinion 252 can cause the driving rack 266 to move proximally. Because the driving rack 266 is meshed with the teeth 280 on the spur gear 278, the spur gear 278 rotate in a counter clockwise direction once the biasing force from the protrusions 295, 297 on the washers 290, 292 is overcome, allowing the spur gear 278 and the washers 290, 292 to rotate in the counter clockwise direction $D_1$ until the protrusions 295, 297 of the washer 290, 292 seat in the recesses formed in the coupler 270 at the next rotational position.

Figure 7B:
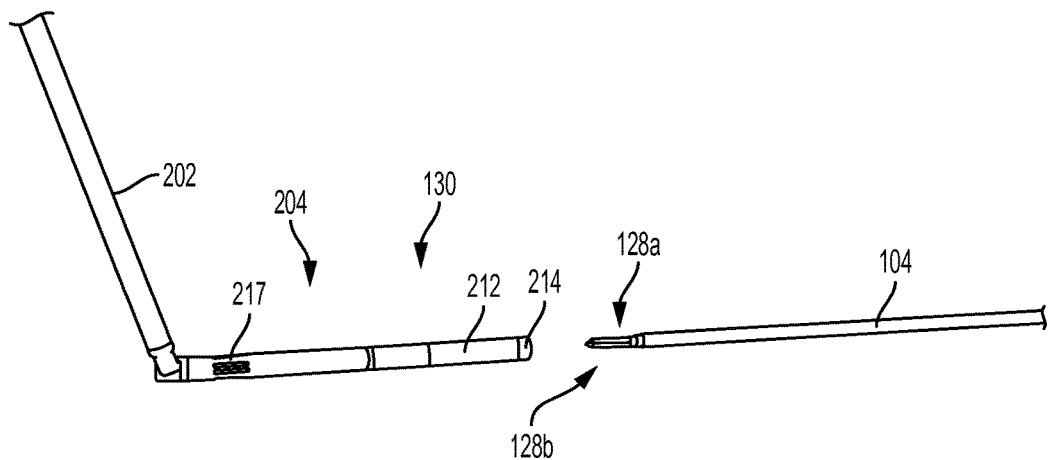
FIG. 7B is a perspective view of the loading device presenting a proximal end of an end effector to the elongate shaft of the surgical device of FIG. 7A.
Figure 7C:
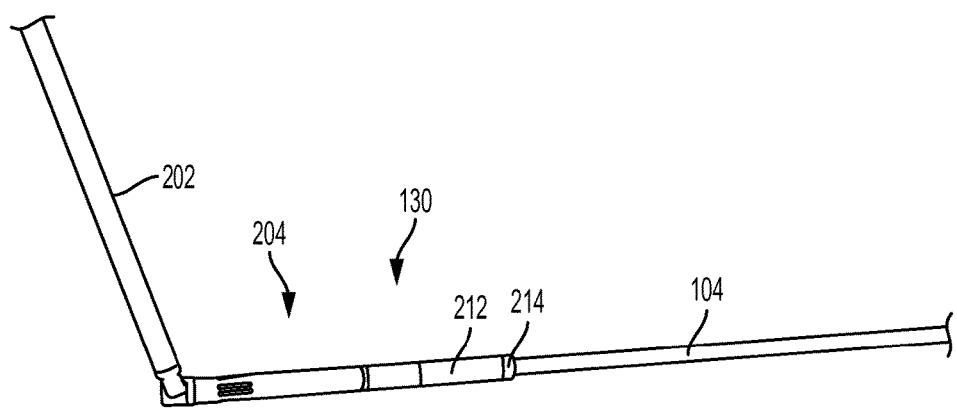
FIG. 7C is a perspective view of the elongate shaft of the surgical device engaging with the end effector on the loading device of FIG. 7B.
Figure 7D:
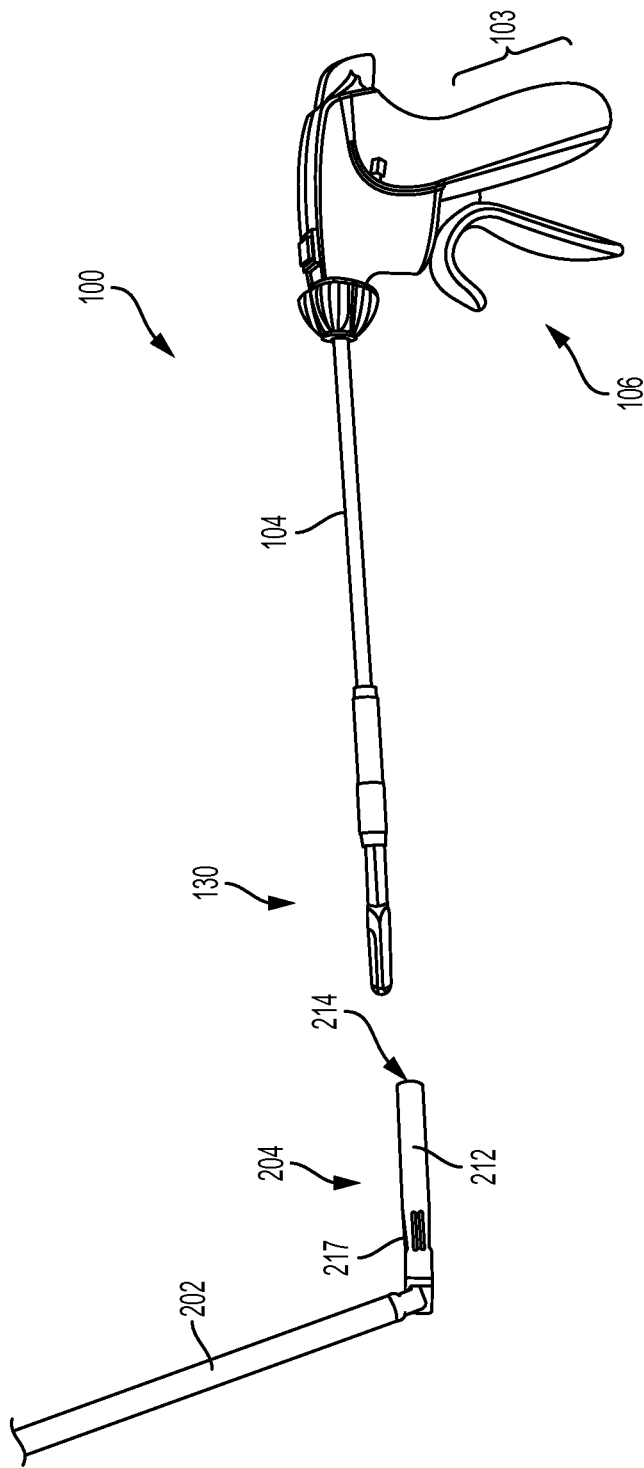
FIG. 7D is a perspective view of the end effector having been removed from the delivery end of the loading device and being coupled to the surgical device of FIG. 7A.

The distal portion 204 of the loader 200 can be articulated relative to the shaft 202 of the loader 200 by moving the slider 206 proximally or distally along the track 214 as needed so as to align the end effector 130 and the attachment mechanisms of the surgical instrument 100, as shown in FIG. 7B. The surgical device 100 can be moved to a ready-to-load position and the distal end 104d of the shaft 104 of the surgical device 100 can be advanced distally toward a proximal end of the end effector 130 until the distal end of the shaft 104 is disposed in the distal portion 204 of the loader 200 as in FIG. 7C. The arms 128a, 128b can deflect medially so as to create a smaller size profile that can fit inside of the end effector's tube 212. After the end effector 130 is disposed on the shaft 104 and engages with the arms 128a, 128b, the end effector 130 locks onto the shaft 104 by the arms 128a, 128b moving radially outward, for instance, by passing the inner shaft 138 distally through the intermediate shaft 128, as described in greater detail in U.S. Patent Application Publication No. 2011/0087267 entitled "Method for Exchanging End Effectors in Vivo," and in U.S. patent application Ser. No. 14/836,069, entitled "Surgical Device Having Actuator Biasing and Locking Features," the contents of which were previously incorporated by reference in their entirety. The device 100 is now in a ready-to-actuate position because the end effector 130 is now coupled to the device 100. With the end effector 130 attached to the device 100, a force can be applied in a proximal direction to the housing 102 of the device 100 to release the engagement features 217 from the end effector 130 and to withdraw the end effector 130 from the loader 200 as in FIG. 7D. Tissue can be then manipulated using the device 100 by actuating the closure actuator 106 of the housing 102 (e.g., moving the closure actuator toward or away from the housing 102) to operate the end effector 130, e.g., open and close the pivot jaws.

In one embodiment, the loader 200 can be removed from the surgical site by withdrawing the housing 208 and the elongate shaft 202 proximally and this can automatically cause the articulating distal portion 204 to move from its second, articulated position to its first, resting position. That is, as the loading device 200 is withdrawn from the patient's body, the anatomy and/or a trocar extending through the incision can overcome the biasing force applied by the washers 290, 292 and can cause the distal articulating portion 204 to pivot back to its resting position in which the distal articulating portion 204 is coaxial with the elongate shaft 202 of the loader 200. In other embodiments, a user can manually articulate the distal portion 204 back to its 0 degree delivery position by retracting the actuator 206.

After completing the surgical procedure using the surgical device 100, the end effector 130 can be detached from the shaft 104 of the surgical device 100 ex vivo or in vivo. If the loader 200 was previously removed, the loader 200 can be reintroduced through the second incision into the surgical field to allow for in vivo detachment of the end effector 130. With the distal articulating portion positioned at a surgical site, the actuator 206 of the loading device 200 can be engaged to change the angle of the articulating distal portion relative to the elongate shaft 202 of the loader 200. The distal end of the end effector 130 can be inserted and seated in the distal end of the loader 200, and the inner shaft 138 and the arms 128a, 128b can be moved proximally to its unlocked position. The end effector 130 can be held in the loader 200 by the engagement feature (not shown) and the distal end of the shaft 104 can then be withdrawn, leaving the end effector 130 in the loader 200 and thereby detaching the end effector 130 from the surgical instrument 100. The loader 200 having the end effector 130 disposed therein can be removed from the surgical field. A different end effector 130 can then be inserted into the loader 200 and then attached to the surgical instrument 100 using the steps described above or the surgical instrument 100 can be withdrawn from the surgical field.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An end effector delivery device, comprising:
an elongate shaft having a lumen formed therein that extends along a length of the elongate shaft;
an articulation rack extending through at least a portion of the lumen of the elongate shaft, the articulation rack having teeth formed thereon;
an articulating delivery end coupled to a distal end of the elongate shaft, the articulating delivery end having a hinge at which a distal portion of the articulating delivery end is configured to pivot with respect to a proximal portion of the articulating delivery end, the distal portion of the articulating delivery end being configured to releasably hold an end effector;
a pinion having teeth meshed with the teeth of the articulation rack, the pinion being coupled to the hinge such that translation of the articulation rack along a longitudinal axis extending through the elongate shaft rotates the pinion to change an angle between the articulating delivery end and the elongate shaft; and
first and second deformable washers having a plurality of protrusions formed on an outer surface thereof that frictionally engage a plurality of recesses formed on inner, opposed surfaces of the proximal portion of the articulating delivery end.

2. The device of claim 1, wherein each washer includes an opening formed therein that defines an inner wall, the inner wall having a plurality of keys projecting therefrom.

3. The device of claim 1, wherein each washer includes a plurality of protrusions spaced apart along an outer surface of each washer and configured such that as the articulation rack is advanced, the plurality of protrusions deform and allow the first and second washers to rotate until the plurality of protrusions frictionally engage recesses of the plurality of recesses that are adjacent to the recesses in which the plurality of protrusions were previously engaged.

4. The device of claim 3, wherein the plurality of protrusions are spaced apart along one hemisphere of the outer surface of each of the first and second washers such that the angle between the articulating delivery end and the elongate shaft has a maximum angle of 90 degrees with respect to the longitudinal axis.

5. The device of claim 1, wherein the first and second washers are offset from the longitudinal axis extending through the elongate shaft.

6. The device of claim 1, further comprising a shaft extending through the pinion and through the first and second washers and configured so that rotating the pinion in a first direction rotates the first and second washers in the first direction.

7. The device of claim 1, wherein the first and second washers are formed from an elastic material.

8. The device of claim 1, further comprising one or more driving pinions coupled to a proximal end of a driving rack, the one or more driving pinions having teeth meshed with the teeth of the driving rack such that rotation of the one or more driving pinions effects translation of the articulation rack along the longitudinal axis.

9. The device of claim 1, further comprising a housing from which the elongate shaft extends, the housing having an actuator configured to translate the articulation rack along the longitudinal axis.

10. An end effector delivery device, comprising:
an elongate shaft having a central longitudinal axis extending along a length thereof and having proximal and distal ends;
a hinge having a proximal portion, a distal portion, and a pivot at which the distal portion of the hinge pivots relative to the proximal portion of the hinge, the proximal portion of the hinge having a proximal end coupled to the distal end of the elongate shaft and having a distal end with first and second opposed arms;
first and second deformable washers having a plurality of protrusions formed on an outer surface thereof that frictionally engage a plurality of recesses formed on inner surfaces of the first and second opposed arms;
an end effector delivery end coupled to the distal portion of the hinge, the end effector delivery end being configured to releasably hold an end effector, wherein an angle between the end effector delivery end and the elongate shaft changes when at least some of the plurality of protrusions of the first and second deformable washers deform and move to different recesses of the plurality of recesses of the first and second opposed arms; and
an articulation rack coupled to a toothed pinion, the toothed pinion being coupled to the pivot such that distal advancement of the articulation rack rotates the toothed pinion and the first and second washers about a central rotational axis of the pivot to adjust an angle between the proximal and distal portions of the hinge.

11. The system of claim 10, wherein each washer includes an opening formed therein that defines an inner wall, the inner wall having a plurality of keys projecting therefrom and spaced radially along the inner wall.

12. The system of claim 10, wherein the plurality of protrusions are spaced apart along one hemisphere of the outer surface of each of the first and second deformable washers such that an angle formed between the proximal and distal portions of the hinge has a maximum angle of 90 degrees with respect to a longitudinal axis of the proximal portion of the hinge.

13. The system of claim 10, wherein the end effector delivery device has an unarticulated position in which the distal portion of the hinge is coaxial with the elongate shaft.

14. The system of claim 13, wherein when the distal portion of the hinge is in an articulated position, a frictional force applied by the first and second deformable washers to the distal portion of the hinge is greater than the frictional force applied by the first and second deformable washers when the distal portion is in the unarticulated position.

15. A surgical method, comprising:
articulating a distal portion of a loading device having an end effector removably coupled thereto relative to an elongate shaft of the loading device using a rack-and-pinion, an angle between the distal portion and the elongate shaft being maintained by a biasing force applied by washers disposed in a hinge coupled between the elongate shaft and the distal portion of the loader; and loading the end effector onto a surgical device, wherein the washers include a plurality of deformable protrusions formed on an outer surface thereof that apply the biasing force to the hinge.

16. The method of claim 15, wherein a plurality of recesses formed in the hinge are engaged by the deformable protrusions when the biasing force is applied, and the deformable protrusions are configured to move to different recesses of the plurality of recesses as the angle between the distal portion and the elongate shaft is adjusted.

17. The surgical method of claim 15, further comprising adjusting the angle formed between the distal portion and the elongate shaft by applying a force via the rack and pinion that is sufficient to overcome the biasing force applied by the washers.

* * * * *